United States Patent
Chen et al.

(10) Patent No.: US 9,533,050 B2
(45) Date of Patent: Jan. 3, 2017

(54) VAGINAL RING INCLUDING MELOXICAM AND AN AGENT FOR MODULATING THE RELEASE OF THE ACTIVE PRINCIPLE, WHICH CAN BE USED AS A CONTINUOUS-USE CONTRACEPTIVE IN WOMEN

(75) Inventors: Shu-Chen Chen, Santiago (CL); Marianela del Carmen Beltran Apablaza, Santiago (CL)

(73) Assignee: LABORATORIOS ANDROMACO S.A., Santiago (CL)

( * ) Notice: Subject to any disclaimer, the term of this patent is extended or adjusted under 35 U.S.C. 154(b) by 72 days.

(21) Appl. No.: 14/367,678

(22) PCT Filed: Dec. 29, 2011

(86) PCT No.: PCT/IB2011/056022
§ 371 (c)(1),
(2), (4) Date: Sep. 12, 2014

(87) PCT Pub. No.: WO2013/098591
PCT Pub. Date: Jul. 4, 2013

(65) Prior Publication Data
US 2015/0328319 A1    Nov. 19, 2015

(51) Int. Cl.
*A61F 6/08* (2006.01)
*A61K 47/32* (2006.01)
*A61K 31/5415* (2006.01)
*A61K 9/00* (2006.01)

(52) U.S. Cl.
CPC .............. *A61K 47/32* (2013.01); *A61F 6/08* (2013.01); *A61K 9/0036* (2013.01); *A61K 31/5415* (2013.01)

(58) Field of Classification Search
CPC ......... A61F 6/08; A61K 47/32; A61K 9/0036; A61K 31/5415
USPC ............................. 424/432; 514/226.5, 841
See application file for complete search history.

(56) References Cited

U.S. PATENT DOCUMENTS 6,086,909 A    7/2000 Harrison et al.

OTHER PUBLICATIONS

Malcolm et al., Advances in microbicide vaginal rings, Antiviral Research 88S (2010) S30-S39.*
El-Badry et al., Enhance of the Dissolution and Permeation Rates of Meloxicam by Formation of Its Freeze-dried Solid Dispersions in Polyvinylpyrrolidone K-30, Drug Development and Industrial Pharmacy, 32:141-150, 2006.*
Digenis et al., Novel Vaginal Controlled-Delivery Systems Incorporating Coprecipitates of Nonoxynol-9.*
Jesam, C., et al., Suppression of Follicular Rupture with Meloxicam . . . , Human Reproduction, vol. 25, No. 2, pp. 368-373, 2010.
Croxatto, H., Meloxicam-Releasing Vaginal Ring: A Non Hormonal . . . , 13th World Congress on Menopause. Roma. 8-11, 2011.
International Search Report issued in PCT Application No. PCT/IB2011/056022.

* cited by examiner

*Primary Examiner* — Michael G Hartley
*Assistant Examiner* — Nabila Ebrahim
(74) *Attorney, Agent, or Firm* — Lucas & Mercanti, LLP

(57) ABSTRACT

The invention relates to a sustained-release vaginal ring which includes meloxicam and an agent for modulating the release of the active principle, such as polyvinylpyrrolidone K-30, which releases the active principle over at least 90 days and which can be used as a continuous-use contraceptive in women. The vaginal ring preferably includes 5 wt % to 30 wt % of meloxicam, relation to total weight of the formulation.

8 Claims, 14 Drawing Sheets

VAGINAL RING INCLUDING MELOXICAM AND AN AGENT FOR MODULATING THE RELEASE OF THE ACTIVE PRINCIPLE, WHICH CAN BE USED AS A CONTINUOUS-USE CONTRACEPTIVE IN WOMEN

CROSS REFERENCE TO RELATED APPLICATION

This Application is a 371 of PCT/IB2011/056022 filed on Dec. 29, 2011 and the application is incorporated herein by reference in their entirety.

The present invention relates to a vaginal ring containing meloxicam, an cyclooxygenase-2 (COX-2) inhibitor and pharmaceutically acceptable excipients modifying active principle release, useful as a continuous-use contraceptive in women, to be administered once a month, every other month or every three months.

STATE OF THE ART

The most common methods for fertility control used today include barrier methods that prevent sperm from entering the uterus, surgical sterilization methods, spermicides methods and altering menstrual cycle with steroidal hormones. As pharmacological method, hormonal contraceptives constitute the quintessential contraceptive method that has been used for more than 50 years in women worldwide. They were developed from the premise of mimic the hormonal changes that occur during pregnancy, which is the physiological period were fertilization does not occur in women. During all this time, various products containing hormones, inducing a temporary sterility have been available to users primarily in the form of oral contraceptive.

Five decades after the introduction of the hormonal contraceptive pill or oral contraceptives (COCs), it remains one of the most used contraceptive methods in family planning worldwide. Currently, over 100 million women have taken the pill. This ranks first among family planning methods in married women in half of the countries surveyed, especially in Western Europe (Population Reports, Series A, No. 9, 2000).

In the past 35 years, there have been significant advances in development of new contraceptive technologies, mainly based on the transition from high to low doses of combined oral contraceptives and the synthesis of new estrogen molecules and mainly progestins. Advances that have caused a great impact are those related to new release systems of sex hormones. Currently, there are different routes of administration for releasing hormones into the body, which are: oral, injectable, implantable, transdermal, intravaginal and intrauterine route. Also the development of controlled-released polymers containing hormones that allow maintenance of constant levels of hormones for very long periods of time is a very important advance.

However, the administration of combined hormonal contraceptives in women, independent of the route of administration, present several disadvantages which have not been overcome and mainly consisting of risks associated with venous thrombosis, heart attacks, strokes, atherogenic effect, increased insulin resistance, gallbladder diseases and liver tumors. In smokers the cardiovascular complications are more apparent and consequently combined hormonal contraceptives are contraindicated in women over 35 who smoke. Another problem is the occurrence of hypertension, reversible once the hormone treatment stop. The hypertension would influence the risk of stroke, and in patients with marginal cardiac reserve this method should not be used because it can trigger accidents due to fluid retention. They are also contraindicated in women with a history of heart attack or embolism, blood clots, stroke, known or suspected cancer, and liver disease; and in women who are with hormonal replacement therapy (perimenopause).

Currently, low-dose oral hormonal contraceptives and the development of new progestogens, aim to deliver a safer therapy than prior pills and as effective as those, so these strategies has been supported looking for a significant reduction of major life risks associated with COCs consumption, including: heart attack, stroke and blood clots generated by deep vein thrombosis of the lower extremities. Even so, health authorities from different countries continue to evaluate the benefits and risks that, for example, represent the use of these new contraceptives, such as progestin drospirenone. Recent studies show the increased risk of suffering a deep vein thrombosis and pulmonary embolism, a potentially fatal condition, in women who use drospirenone combined with estradiol.

Moreover, the contraceptive effectiveness also depends on the systemic administration of COC, in such a manner that an omission can cause an unexpected pregnancy. Clinical studies indicate that with proper use, the pregnancy rate is 0.1% in the first 12 months of use. However, the results of statistics compiled in 21 countries show that rate ranges between 1.7% (Bangladesh) to 10.5% (Bolivia), indicating that the COC has not been used in the right way to achieve the projected contraceptive efficacy. Meanwhile, contraceptive vaginal rings containing hormones, such as NuvaRing®, commercially available, also have a compliance variable in the administration by the user. It is designed to be used during a cycle; a cycle comprises 3 weeks of ring use followed a period of 1 week without ring. Once inserted, the ring should remain in place for 3 weeks, and then removed the same "day" of the week that was inserted; this implies the need for the user to recall the day of ring removal and the "uncertainty" generated when is removed late by oversight. Alternatively, the user can decide for a cycle with no menstruation, for which the ring should be immediately replaced by another after its retirement at three weeks.

There is a need for pharmacological alternatives to the currently existing in contraception. Contraceptive methods that provide highly effective protection and, at the same time, produce fewer side effects, which can be used by women living in risk of thromboembolism, or women who are under hormone replacement therapies (perimenopause) are needed. In addition, there is a need for them to be easy to use for reducing to a minimum the factor of ineffectiveness and/or uncertainty due to oversight or delay in the administration and/or removal of the same, in the case of vaginal rings or devices.

The female reproductive system comprises ovaries, fallopian tubes, uterus, cervix and vagina. In the ovary a group of follicles called primary follicle are recruited, in an early phase of the menstrual cycle of women and under the stimulus of gonadotropins. Subsequently, on day 6 of the cycle, one of these follicles reaches the mature or dominant phase. The follicles not destined to ovulate, degenerate, while the oocyte in the primary follicle is arrested in prophase of meiosis (Carr and Wilson, 1991).

The term ovulation refers to the release of one or more eggs or mature oocytes from follicles. It is characterized by specific hormonal changes. Happen just prior to the increase of luteinizing hormone (LH) and follicle stimulating hormone (FSH) levels, and the decrease in estrogen levels.

Immediately prior to ovulation a pre-ovulatory increase of LH triggers the final step of ovulation, resumption of oocyte meiosis (Tsafriri and Adashi, 1996) followed by the rupture of the follicular wall that allows the mature follicle to be released. A morphological expression of oocyte maturation is the expansion of the cells of the granulose surrounding the follicle (cumulus expansion) and the dissolution of germinal vesicles. If this final oocyte maturation is prevented or damaged, the oocyte cannot be fertilized by a sperm. Therefore, the expansion of the cluster is an obligatory step for the success of ovulation and fertilization, which is regulated by prostaglandins, specifically $PGE_2$. The selectivity of this regulatory step is demonstrated by the observation that the expression of the enzyme required for the synthesis of prostaglandins, cyclooxygenase-2 (COX-2), is triggered about 10 hours before ovulation in various mammalian species (Sirois and Dore, 1997).

Cumulus cells from cumulus-oocyte complex produce prostaglandins induced by COX-2 and also other prostaglandins (Jick S et al., 2006). During the pen-ovulatory period, the expression of a set of genes in cumulus cells are critical for normal ovulation and for a normal fertility rate. It has also been observed that between the first induced genes for production of prostaglandins, is COX-2, which has a limited rate for the same enzyme (Sirois J et al., 1993, Wong W Y at al., 1992). It has been proposed that COX-2 is part of a molecular clock that sets the species-specific time when ovulation occurs (Sirois J et al., 2004). This suggestion is supported by results obtained from studies in macaque monkeys. In this species, the timing of prostaglandin secretion is dependent on the induction of COX-2, microsomal prostaglandin E synthase and more particularly, to the expression and post-transcriptional activation of phospholipase A2 in granulose cells (Duffy D M et al., 2005). These mechanisms positions strict controls on the processes required for the synthesis of prostaglandins and the time of ovulation.

In general, it is believed that COX-2 presence is induced by, among others, inflammatory processes of cell proliferation and differentiation. In mice, full mutation of COX-2 gene results in defective cumulus expansion and a reduced ovulation rate and infertility (Dinchuk J E et al., 1995; Lim H et al., 1997; Davis B J et al., 1999; Ochsner S A et al., 2003b). Similarly, in rats and mice, both treatments with indomethacin, a non-selective COX inhibitor, as NS-398, a selective inhibitor of COX-2, also block ovulation and expression of TSG-6 gene (Mikuni Metal., 1998; Yoshioka S et al., 2000; Espey L L et al., 2002). In rhesus monkeys was observed that the intrafollicular injection of indomethacin, just before ovulation occurs (1 day after LH surge), can prevent the release of the oocyte being trapped inside the follicle (Duffy and Stouffer, 2002) and it has been reported that the expression of COX-2 and $PGE_2$ concentrations are increased in follicular fluid prior the time of expected ovulation in rhesus monkeys (Duffy y Stouffer, 2001).

Inhibition of ovulation has been observed in rabbit receiving a single dose of meloxicam intraperitoneally, a selective inhibitor of COX-2, in a dose-dependent manner and depending of the post-mating time when it was administered, as reflected by a decrease in pregnancy rate (Salhab A S et. al., 2001). A 100% of contraceptive effect was observed in those animals receiving meloxicam prior ovulation at doses of 20 mg/kg; however, pregnancy occurred in those rabbits that received meloxicam post ovulation, even in high doses. These results show that the meloxicam in a single dose acts in rabbit ovulation and allow ruling out effects on reproductive stages including fertilization, decidualization and implantation. It was observed that inhibition of ovulation also take place when meloxicam is administered orally, intravaginally and rectally (Salhab A S et al., 2003). Additionally the intravaginal administration of meloxicam prevents pregnancy in rabbits when it was administered post-mating in the form of suppositories at a dosage of 40 mg for one time. Some rabbits expelled the suppository and on those pregnancy was observed. Contraceptive effect was also observed in 100% of rabbits given meloxicam orally.

In 1996 two reports showed the of nonsteroidal anti-inflammatory drugs (NSAIDs) effect in women who were continuously taking naproxen, piroxicam, diclofenac or indomethacin orally for the treatment of chronic inflammatory diseases (Smith et al., 1996; Akil et al., 1996). Ovulatory deficiency and infertility was observed in these patients, conditions that were revert upon NSAIDs discontinuation, and as a result, all patients were pregnant. As early as 1987, Killick and Elstein showed that indomethacin induced abnormal and delayed follicular rupture, condition known as LUF (luteinized unruptured follicle); what was confirmed as the cause of infertility in patients taking NSAIDs (Smith et al., 1996; Akil et al., 1996). Indomethacin treatment also delayed by 2-12 days ovulation in women (Athanasiou S. et al.., 1996) and the COX-2 selective inhibitor, rofecoxib, had a similar effect.

In 2001, Pall et al., conducted a randomized double-blinded study with rofecoxib in women between 30 and 40 years old. 25 mg of oral rofecoxib (in 6 female) or placebo (in 7 females) were administrated when the dominant follicle reached a diameter of 14-16 mm, once daily for 9 consecutive days. Follicle size was monitored and serum hormone analysis was also performed. In 4 of the 6 women who received rofecoxib was observed delay in the late follicular rupture, compared with the placebo group. There was no difference in peripheral serum concentrations of progesterone, estradiol, LH and FSH, among both treatment groups. These results suggest that the ovulation process can occur despite a reduced intrafollicular concentration of prostaglandin concentration but the process efficiency is damaged. In this study, rofecoxib in the doses tested, was not sufficient to inhibit ovulation.

It has been observed that in cycles treated with meloxicam and levonorgestrel combination, the lack of follicular rupture is higher than in cycles treated with levonorgestrel alone. It was noted that joint therapy prevents ovulation in a high proportion of cases than levonorgestrel alone (Massai et al., 2007).

A clinical study of meloxicam addressed to study its effect on women ovulation, reversibility and tolerability was published in 2006 (Bata et al., 2006). A double-blind, placebo-controlled crossover study was designed. The study lasted four menstrual cycles. The highest dose of meloxicam (30 mg/day) utilized in the treatment of rheumatoid arthritis was used for five consecutive days. In the group treated with meloxicam a delay of 5 days in the follicular rupture was observed, an increase of 55% in the maximum diameter of the follicle and a 33.5% decrease in plasma progesterone level. The observed effects were reversible.

In 2010, Jesam et al., published a study where they evaluated daily follicular growth in women who received meloxicam for 5 days, from the day when the dominant follicle reached a diameter of 18 mm. The results showed that the meloxicam at 30 mg doses administered for 5 days in the late follicular phase, was more effective in delay ovulation than at a dose of 15 mg. Follicular rupture was delayed for more than 48 hours in 11 of 22 cycles (50%) in the group treated with 15 mg/day and in 20 of 22 cycles (91%) in the group treated with 30 mg/day. On all the cycles with ovulatory dysfunction (delayed ovulation) levels of estradiol comparables with ovulatory cycles were observed. All women had normal progesterone levels during the luteal phase and there was no difference in the maximum values of progesterone at this stage between the two doses of meloxicam. Ovulation dysfunction was observed in 100% of the cycles when 30 mg meloxicam were administered before the beginning of the LH surge and only was 46% at doses of 15 mg; however, there was no significant difference between doses when the administration was performed after the LH surge.

From the evidence presented, it has been suggested that meloxicam could be useful as a "emergency" contraceptive (Pazos A. et al., Trabajo de Grado, Biblioteca del Claustro, Universidad del Rosario, Colombia, June 2010, http://hdl.handle.net/10336/1959), i.e., its oral administration after a sexual relationship would avoid a functional ovulation and therefore fertilization. However, according to existing evidence, this effect depends of the stage of the menstrual cycle of the woman, because if the meloxicam is given when the follicle has already been released, there is no contraceptive effect and fertilization will occur. When administered meloxicam in the preovulatory stage, ovulation is delayed or completely inhibited, and if ovulation occurs after that delay, it will occur late, when the oocyte is no longer fecundable due to the stage of cellular development in which is located. It has not been shown that meloxicam interacts in other stages of fertilization.

It would be useful to have a meloxicam administration effective as a contraceptive, independent of the stage of the cycle when intercourse occurred. An alternative is the continuous oral administration of meloxicam for the entire cycle of women, however the side effects of NSAIDs on the gastric mucosa are known, especially in prolonged therapy can lead to bleeding, ulcerations and perforations of the upper gastrointestinal tract, reduction of renal function and as a result fluid retention and marked hypertension. Cardiovascular risks as thrombotic events and myocardial infarction should also be considered. These risks may increase with prolonged use of NSAIDs.

Considering this, emerges the possibility of using a route of administration different than the oral route to minimize the side effects caused by oral ingestion of NSAIDs, as meloxicam, in a continuous and/or long-term treatment.

The present invention relates to an alternative route to oral administration, specifically intravaginal route for administration of meloxicam together with a enhancer of active agent release. With this formulation becomes possible to obtain low plasma levels of the drug after its administration into the vagina, even when local uptake and release of the active agent increase.

Different pharmaceutical forms for administering drugs intravaginally have been described, such as suppositories, solutions, creams, foams, gels, tablets and vaginal rings. Intravaginal delivery systems are described in patents and patent applications: U.S. Pat. No. 6,086,908, US20050276836, U.S. Pat. No. 6,086,909, EP0889724, U.S. Pat. No. 7,004,171, WO2004095161 and US20050276836, intravaginal release systems are described and between the alternatives vaginal rings are mentioned. However, none of these documents specifically details a ring comprising meloxicam and a release enhancer.

In the pharmaceutical industry the development of vaginal rings for the delivery of different types of active principles have been addressed, but only some of them comprising hormones have become part of the therapeutic arsenal for human use. This is because efficacy and safety have only been demonstrated for a few products in the form of vaginal rings, which have made them worthy of approval by the health authorities in different countries. These rings are used as contraceptives in monotherapy (Progering®, progesterone), combination therapy (NuvaRing®, ethonogestrel y ethinylestradiol), hormone replacement therapy with estradiol in the treatment of menopausal symptoms (Estring®, Femring®) and as a luteal supplement in women requiring exogenous progesterone for oocyte donation recipients in infertility cases, in vitro fertilization, embryo transfer and other assisted reproduction techniques (Fertiring®).

In U.S. Pat. No. 6,086,909 are described intravaginal devices useful for the treatment or prevention of dysmenorrhea containing an active principle selected from non-steroidal anti-inflammatory agents, prostaglandin inhibitors, COX-2 inhibitors, local anesthetics, among others. Meloxicam is mentioned as one the COX-2 inhibitors. It is further stated that it can be used in vaginal suppositories in doses of 7.5 mg. In the Specification of U.S. Pat. No. 6,086,909 is mentioned that vaginal rings consist of an inert elastomer ring coated by another layer of elastomer containing the drug to be released and optionally containing a third outer layer of elastomer containing no drug that controls the release rate. No specific examples of a pharmaceutical product in the form of vaginal rings comprising meloxicam are described.

In U.S. Pat. No. 6,951,654 is mentioned that the drug release from rings formed by a homogeneous pattern or matrix, in which the active agent is homogeneously distributed in an elastomeric system, provides a release with a first order, exponential decay characterized by a high initial release of drug followed by a slower release, indicating that the drug cannot be released with a substantially constant or controlled release rate (zero-order). In U.S. Pat. No. 6,951,654 intravaginal drug release systems are described, substantially a first order release during the first 24 hours, followed by at least three days of zero order release. Rings comprising an antimicrobial agent and agents that enhance the release of the active agent, such as polyvinylpyrrolidone, cellulose ethers, polyacrylic acid, carbomer, alginic acid, sugars such as lactose, cyclodextrins, among others are mentioned. Among the results showing cumulative drug release until day 25, is observed that at the same dose, 50 mg of metronidazole (MET), rings with 5% and 10% polyvinylpyrrolidone (PVP) released more amount of drug than rings without PVP over the 25 days period. Compared with higher doses different behavior is observed (U.S. Pat. No. 6,951,654, FIG. 3). In the first three days the release from vaginal rings containing PVP and 50 mg of metronidazole (MET) is slightly higher than from the rings containing higher dose of the active agent (100 mg MET) with no PVP. From day 6 begins to decrease the release from PVP rings, becoming lower than that of the systems that do not contain the agent (100 mg MET). From day 13, the cumulative release of the rings with PVP is significantly lower than from the rings with double dose but with no PVP. In U.S. Pat. No. 6,951,654 is observed that the addition of PVP or lactose to the rings induces higher release of antiseptics, but this increase is not sustainable over time and also does not exceed the highest dose release of the active principle, which does not comprise PVP, over time.

DETAILED DESCRIPTION OF THE INVENTION

There is a need for an effective and safe method of contraception so that it can be administered in a wide range of patients, without excluding age and/or pathologies inherent to age.

The present invention relates to a non-hormonal contraceptive product for continuous use that can be used for both young women and women who are in the perimenopause. Also refers to a product that is administered once a month, self-regulated through the normal menstrual cycle of each woman, minimizing the risk of ineffectiveness for the non-compliance factor of user-dependent therapy, because is not necessary to recall when administering or removing the product, since the menstrual cycle itself indicate.

More specifically, the invention relates to a vaginal ring comprising meloxicam for administration in women without the pharmacological risks that involved a hormonal contraceptive therapy of continues use. Furthermore, with ring transvaginal administration the side effects associated to long term oral administration of a COX-2 inhibitor are minimized.

Using meloxicam vaginal ring of the present invention as continuous contraception method, the oocyte function blockage is achieved without interfering with the reproductive hormonal environment or with the normal menstrual cycle. Therefore, since the menstrual cycle and ovulation does not alter with COX-2 inhibition, the hypothalamic-pituitary-gonadal axis will not be altered by administration of a vaginal ring with meloxicam. This offers significant advantages over administration of conventional steroidal contraceptives as side effects associated with the alteration of hormone physiological parameters are reduced or completely avoided.

The solution of the present invention consists of a vaginal ring comprising meloxicam along with a release modifier, with the objective of increasing the tissue concentration of the active principle without significantly increasing plasma levels of the same.

It has been found that only vaginal rings containing PVP K-30 showed a release profile favoring tissue concentration increase of the drug while maintaining low plasma levels throughout the entire period of treatment. This effect was not observed using other release enhancers known in the prior art. PVP K-30 corresponds to the polymer of 1-vinyl-2-pyrrolidone, or polyvinylpyrrolidone, with viscosity in 1% solution (or K value) between 26 and 35 centistokes.

More preferably a vaginal ring comprising meloxicam and a drug release enhancer, specifically PVP K-30, is presented. Surprisingly it has been found that administering vaginal rings with meloxicam and PVP-K30, the endometrial concentration of meloxicam increases, without affecting the plasma concentration of the drug, compared with administration of a vaginal ring with the same concentration of meloxicam but with no PVP-K30. This ensures a therapeutic concentration in the target tissue while keeping low plasma concentrations, ensuring therapeutic effect and decreasing the probability of known NSAIDs systemic side effects and specifically of COX-2 inhibitors.

EXAMPLES OF APPLICATION OF THE INVENTION

1.—Vaginal Rings Comprising Meloxicam

Figure 1:
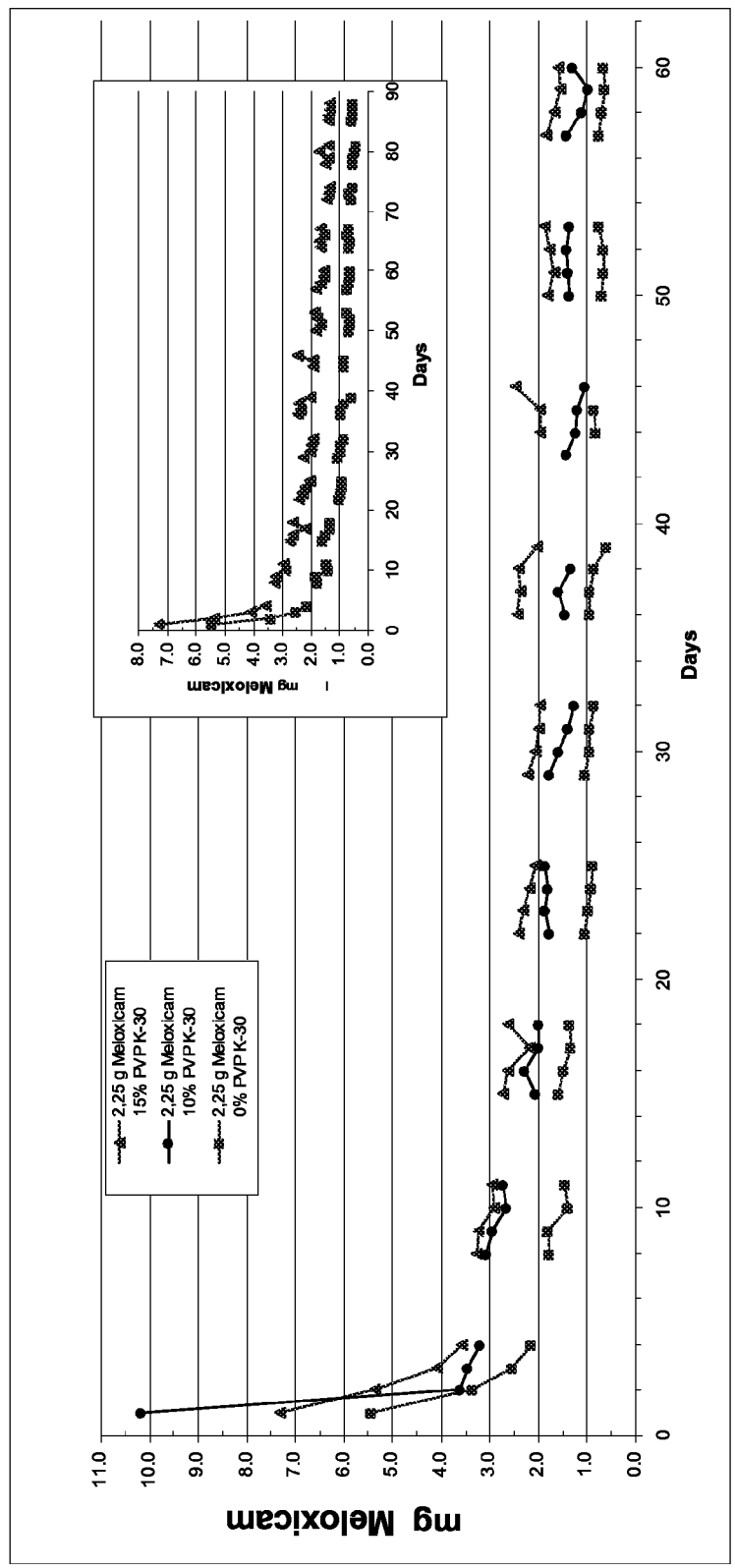
FIG. 1.—In vitro release profile of meloxicam from vaginal rings comprising 2.25 g of meloxicam with no PVP K-30 or 10% and 15% PVP K-30.

Vaginal rings comprising different amounts of meloxicam with a release-modulating agent of the active principle were made, selected from:

PVP K-30: Polyvinylpyrrolidone K-30 or polymer of 1-vinyl-2-pyrrolidone having a viscosity from 26 to 35 centistokes (K value between 26 and 35) in 1% solution Sodium lauryl sulfate Cremophor RH40: Ethoxylate hydrogenated castor oil (CAS 61788-85-0)

AA-1 polycarbophil: acrylic acid polymer crosslinked with divinyl glycol 1 (CAS 9003-97-8)

Lactose

Microcrystalline cellulose.

1.1.—Formulations Tested

In Tables 1 and 2 General Formulations (GF) tested are detailed. Polymers used together with various release modifiers are included.

TABLE 1

Vaginal rings formulations containing meloxicam and PVP K-30

| INGREDIENT | % W/W | | | |
|---|---|---|---|---|
| | GF-1 | GF-2 | GF-3 | GF-4 |
| Polymer A: | | | | |
| Polydimethylsiloxane-vinyl block polymer + amorphous silica (25%) + platinum catalyst | 57.0-80.0 | 62.0-75.0 | 53.0-65.0 | 47.0-65.0 |
| Polymer B: | | | | |
| Dimethyl methyl hydrogen siloxane copolymer (20%) + polydimethylsiloxane | 8.0-10.0 | 8.0-10.0 | 7.0-10.0 | 7.0-10.0 |
| meloxicam | 10.0-35.0 | 5.0-25.0 | 5.0-30.0 | 10.0-35.0 |
| PVP K-30 | 0 | 5.0-10.0 | 10.0-20.0 | 10.0-15.0 |

TABLE 2

Vaginal rings formulations containing meloxicam and release modifiers of the active principle other than PVP K-30

| INGREDIENT | % W/W | | | | | |
|---|---|---|---|---|---|---|
| | GF-5 | GF-6 | GF-7 | GF-8 | GF-9 | GF-10 |
| Polymer A: | | | | | | |
| Polydimethylsiloxane-vinyl block polymer + amorphous silica (25%) + platinum catalyst | 62.9-74.0 | 61.0-75.0 | 55.0-72.0 | 53.0-65.0 | 58.0-65.0 | 0 |
| Polymer B: | | | | | | |
| Dimethyl methyl hydrogen siloxane copolymer (20%) + polydimethylsiloxane | 7.0-10.0 | 8.0-10.0 | 8.0-10.0 | 7.0-10.0 | 7.0-10.0 | 0 |
| Polymer C: | | | | | | |
| Polydimethylsiloxane with terminal hydroxyl group | 0 | 0 | 0 | 0 | 0 | 68.8-81.0 |
| Polymer D: | | | | | | |
| Tetra-n-propyl-silicate Si(OC3H7)4 | 0 | 0 | 0 | 0 | 0 | 1.0-3.0 |
| stannous octoate Sn(C8H15O2)2 | 0 | 0 | 0 | 0 | 0 | 0.2-1.0 |
| Meloxicam | 15.0-30.0 | 10.0-30.0 | 10.0-30.3 | 10.0-30.0 | 10.0-30.0 | 15.0-30.0 |
| Sodium lauryl sulfate | 0.1-1.0 | 0 | 0 | 0 | 0 | 0 |
| Cremophor RH40 | 0 | 1.0-5.0 | 0 | 0 | 0 | 0 |
| AA-1 Polycarbophil | 0 | 0 | 7.0-8.0 | 0 | 0 | 0 |
| Lactose | 0 | 0 | 0 | 10.0-15.0 | 0 | 0 |
| Microcrystalline cellulose | 0 | 0 | 0 | 0 | 5.0-15.0 | 0 |

Various formulations assays were performed to obtain rings to adequately polymerize or cured with the necessary amounts of the active principle in the presence of a release-modulating agent. Rings containing Cremophor RH40 (General Formula 6, GF-6) or polycarbophil (General Formula 7, GF-7) did not cure, so that these agents were discarded. Other rings listed in Tables 1, and 2 polymerized under assay conditions.

Manufactured rings had a weight between 6.0 to 10.5 grams, which varies according to ring thickness. Rings with outer diameter from 54 to 58 mm and cross section between 3 to 6 mm were fabricated.

1.2.—Procedure for Manufacturing Vaginal Rings

A homogeneous blend of all the ingredients to be injected into the ring molds was prepared. First the required amounts of each ingredient were weighed: Polymer A, release modifier agent, if applicable, and meloxicam. These ingredients were mixed until homogenization and the polymer B was added under constant mixing. The mixture was injected into ring molds at room temperature and then kept in an oven at 105° C. for 1 hour. Subsequently molds were cooled and the formed rings were disassembled from their respective molds obtaining the final product.

Rings were also made with other polymers, which were prepared by weighing each ingredient, as noted above, but replacing the polymer A with polymer B, and polymer C was replaced by polymer D, as indicated in Table 2 (GF-10). Additionally stannous octoate was added as catalyst for the polymerization reaction between polymers C and D. The ingredients were mixed until reaching homogeneity and were injected into ring molds. They remained at room temperature (23-25° C.) for 1 hour. The formed rings were then disassembled from their respective molds obtaining the final product.

1.3.—Preferred Formulations of the Present Invention

According to General Formulations of Tables 1 and 2, formulations of vaginal rings comprising different amounts of meloxicam and drug release enhancers were prepared. Preferred formulations of the present invention are included in Tables 3, 4, 5 and 6. All ingredient amounts are expressed in grams.

TABLE 3

Pharmaceutical formulations of vaginal rings with meloxicam containing PVP K-30

| Specific Formulas | Polymer A | Polymer B | Meloxicam | PVP K-30 |
|---|---|---|---|---|
| SF-1 | 8.0 | 1.0 | 1.0 | 0 |
| SF-2 | 7.5 | 1.0 |  | 0.5 |
| SF-3 | 7.0 | 1.0 |  | 1.0 |
| SF-4 | 6.5 | 1.0 |  | 1.5 |
| SF-5 | 6.3 | 0.7 |  | 2.0 |
| SF-6 | 7.75 | 1.0 | 1.25 | 0 |
| SF-7 | 7.25 | 1.0 |  | 0.5 |
| SF-8 | 6.75 | 1.0 |  | 1.0 |
| SF-9 | 6.25 | 1.0 |  | 1.5 |
| SF-10 | 5.85 | 0.9 |  | 2.0 |
| SF-11 | 7.25 | 1.0 | 1.75 | 0 |
| SF-12 | 6.75 | 1.0 |  | 0.5 |
| SF-13 | 6.25 | 1.0 |  | 1.0 |
| SF-14 | 5.75 | 1.0 |  | 1.5 |
| SF-15 | 52.5 | 1.0 |  | 2.0 |
| SF-16 | 6.75 | 1.0 | 2.25 | 0 |
| SF-17 | 6.25 | 1.0 |  | 0.5 |
| SF-18 | 5.95 | 0.8 |  | 1.0 |
| SF-19 | 5.25 | 1.0 |  | 1.5 |
| SF-20 | 6.0 | 1.0 | 3.0 | 0 |
| SF-21 | 5.5 | 1.0 |  | 0.5 |
| SF-22 | 5.1 | 0.9 |  | 1.0 |

TABLE 4

Pharmaceutical formulations of vaginal rings with meloxicam containing sodium lauryl sulfate (SLS)

| Specific Formulas | Polymer A | Polymer B | Meloxicam | SLS |
|---|---|---|---|---|
| SF-23 | 6.74 | 1.0 | 2.25 | 0.01 |
| SF-24 | 6.7 | 1.0 |  | 0.05 |

TABLE 5

Pharmaceutical formulations of vaginal rings with meloxicam containing lactose

| Specific Formulas | Polymer A | Polymer B | Meloxicam | Lactose |
|---|---|---|---|---|
| SF-25 | 6.35 | 0.9 | 1.75 | 1.0 |
| SF-26 | 5.85 | 0.9 |  | 1.5 |
| SF-27 | 5.85 | 0.9 | 2.25 | 1.0 |
| SF-28 | 5.35 | 0.9 |  | 1.5 |

TABLE 6

Pharmaceutical formulations of vaginal rings with meloxicam containing microcrystalline cellulose

| Specific Formulas | Polymer A | Polymer B | Meloxicam | Microcrystalline cellulose |
|---|---|---|---|---|
| SF-29 | 6.95 | 0.8 | 1.75 | 0.5 |
| SF-30 | 5.95 | 0.8 |  | 1.5 |
| SF-31 | 6.45 | 0.8 | 2.25 | 0.5 |
| SF-32 | 5.45 | 0.8 |  | 1.5 |

2.—In Vitro Release Studies

In vitro release studies with the vaginal rings described in Tables 1 to 6 were performed according to the following analytical procedure. In the description of results for the formulations assayed nomenclature of Tables 3 to 6 will be used, as "SF-n", where n is the number of the formulation listed in these tables.

a) Diffusion medium preparation: 189 ml of Zephiran® (17% Benzalkonium chloride) were precisely measured, transferred to a polyethylene container with key containing 24 liters of distilled water. It was stirred to homogenize. The container was labeled assigning a preparation batch number and date of manufacture.

Once prepared diffusion medium, solution was checked by measuring absorbance at 262.4 nm, and the resulting reading should range between 1.3-1.6; otherwise the solution should be discarded.

b) Sample preparation: 4 rings of each formulation selected at random were individually weighed, taking note of the respective weight. Each of the rings was attached with a polyethylene thread of suitable length to allow submerge the rings completely. Rings were suspended in 500 mL wide-mouth polyethylene bottle with screw-cap (to prevent loss of diffusion medium); the rings were fixed with tape on the outer surface of the bottles, so that they were at 2.0±0.2 cm from each bottle bottom. Bottles were labeled with its corresponding ring.

Bottles with samples were placed in a constant temperature water bath (BT-47 Model, Yamato, Japan), setting temperature at 37° C., and operating stirring system at 100 rpm. The bath temperature and stirring speed was checked every day. The temperature should be between 37±0.5° C. and the stirring speed within 100±5 rpm.

Medium solutions were change every day (after 24 hours), except on Sunday. From the second week Monday samples were discarded. Note that diffusion medium was replaced every day at the same time.

c) Analytical procedure: Prepared samples and taken samples are determined by UV spectrophotometry at 355 nm.

A calibration curve with different concentrations of micronized DHEA on diffusion medium was made in order to determine the range of concentrations that meets the Beer-Lambert Law. Standard concentrations to be prepared were defined, and, when necessary, samples dilutions were made.

d) Preparation of standard solutions of meloxicam: About 15 mg of meloxicam standard were precisely weighed in a 100 mL volumetric flask, about 30 mL of dimethylformamide were added, sonicated for 5 minutes, then added 2.0 mL of water and 25 mL of phosphate buffer pH=7.2. It was stirred and diluted with phosphate buffer. An aliquot of 5.0 mL was taken, transferred to volumetric flask of 50 mL and brought to volume with diffusion medium. It was filtered through a 0.45 μm membrane filter. (C=0.015 mg/mL).

We proceed to measure absorbance of taken samples and prepared standards at 335 nm.

The amounts of meloxicam released daily were calculated using the following formulas:

$$\text{Absorbance factor} = \frac{\text{Standard Concentration} \times \text{Diffusion Medium Volume (400 mL)}}{\text{Mean Standard Absorbance}}$$

$$\text{mg Meloxicam} = (\text{Absorbance Factor}) \times (\text{Sample Absorbance})$$

Results of in vitro release assays for vaginal rings comprising meloxicam and a drug release modifier are described below.

2.1. Equal Doses of DHEA (2.25 g) at Different Concentrations of PVP K-30

FIG. 1 shows that the rings containing 2.25 g of meloxicam in the absence of PVP K-30 (SF-16) had an average initial release (day 1) of 5.46 mg of meloxicam (see also Table 7). The initial release from rings containing 10% (SF-18) and 15% (SF-19) PVP K-30 was higher than in the absence of this agent, achieving values of 7.31 and 10.19 mg, respectively. Similarly, rings containing 5% PVP K-30 (SF-17), also had higher release than rings without this agent, achieving values of 6.11 mg (Table 7) on day 1 at equal dose of meloxicam (2.25 g). During the first 4 days, the more pronounced release is maintained for rings with PVP K-30, although a quite pronounced initial decrease occurs in all cases (see FIG. 1).

In Table 7 are listed mean amounts of meloxicam released during the first 4 days from rings containing PVP K-30 at the listed concentrations. For each condition quadruplicate samples of release media of four rings were taken.

TABLE 7

Mean meloxicam release from rings comprising 2.25 g of meloxicam in accordance with the Specific Formulas (SF) listed in Table 3

| | Mean meloxicam release (mg) | | | |
|---|---|---|---|---|
| Days | SF-16 0% PVP K-30 | SF-17 5% PVP K-30 | SF-18 10% PVP K-30 | SF-19 15% PVP K-30 |
| 1 | 5.46 | 6.11 | 10.19 | 7.31 |
| 2 | 3.37 | 4.71 | 3.6 | 5.36 |
| 3 | 2.54 | 4.15 | 3.47 | 4.09 |
| 4 | 2.17 | | 3.19 | 3.59 |
| Mean Release Days 1-4 | 3.39 | 4.99 | 5.11 | 5.09 |

Figure 5:
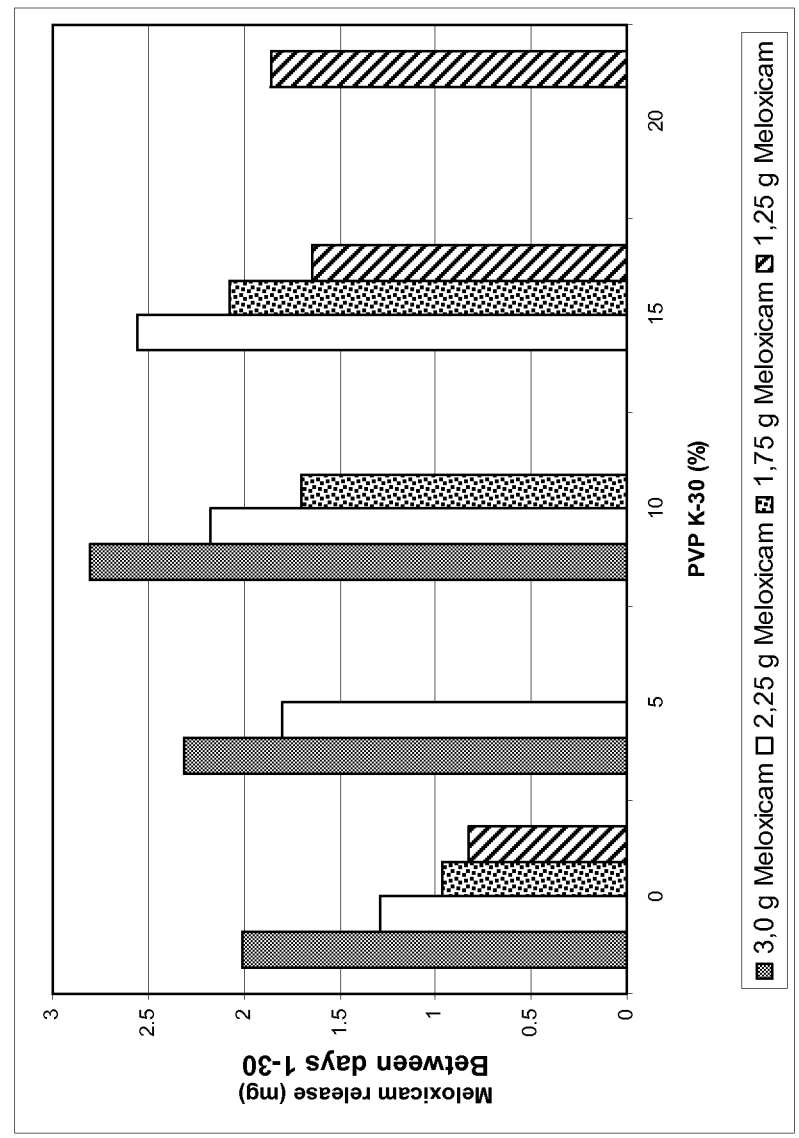
FIG. 5.—Profile of mean in vitro release of meloxicam between days 5 to 30 from vaginal rings comprising 3.0 g, 2.25 g, 1.75 g and 1.25 g of meloxicam with no PVP K-30 or 5%, 10%, 15% and 20% PVP K-30.
Figure 6:
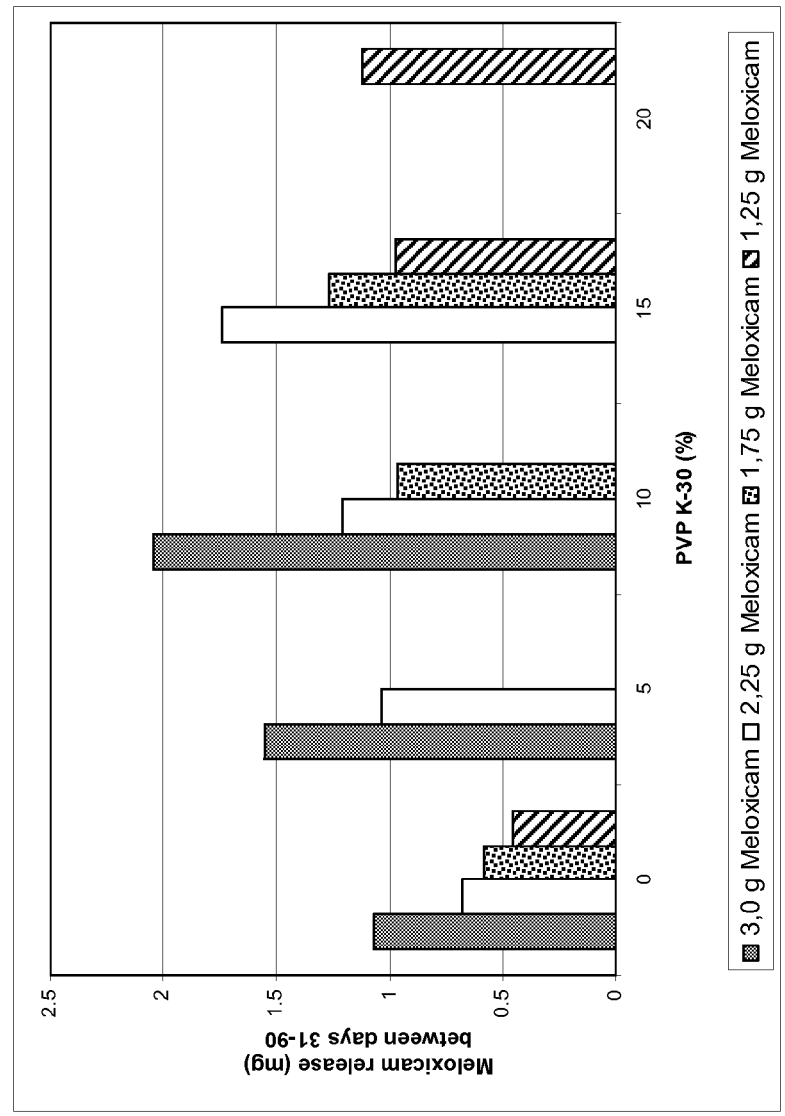
FIG. 6.—Profile of mean in vitro release of meloxicam between days 31 to 90 from vaginal rings comprising 3.0 g, 2.25 g, 1.75 g and 1.25 g of meloxicam with no PVP K-30 or 5%, 10%, 15% and 20% PVP K-30.

From day 8, the slope of the release curve is much lower and the rings continue to release meloxicam constantly and permanently over time, which is maintained until day 90 (insert box FIG. 1). It was also observed that the release of meloxicam over extended periods of time was always higher in the rings containing PVP K-30, clearly evident from FIG. 1 and in the insert box, when comparing rings with equal doses of meloxicam (2.25 g) with no PVP and with 10% and 15% PVP K-30, being even higher in those rings with more amount of this agent. In 15% PVP K-30, the mean meloxicam release between days 5-30 was 2.6 mg; whereas at 10% the mean was 2.17 mg, at 5% was 1.8 mg, and in the absence of PVP K-30 was 1.29 mg (FIG. 5, white bars). It is remarkable to observe that the release of meloxicam remained even until 90 days maintaining the tendency observed in shorter periods of time; so it can be seen that mean meloxicam release between days 31-90 in the presence of 15% PVP K-30 was 1.74 mg; whereas at 10% the mean was 1.21 mg, at 5% was 1.04 mg and in the absence of PVP K-30 was 0.68 mg (FIG. 6, white bars).

2.2.—Low Doses of Meloxicam in the Absence and Presence of Various Concentrations of PVP K-30

Figure 2:
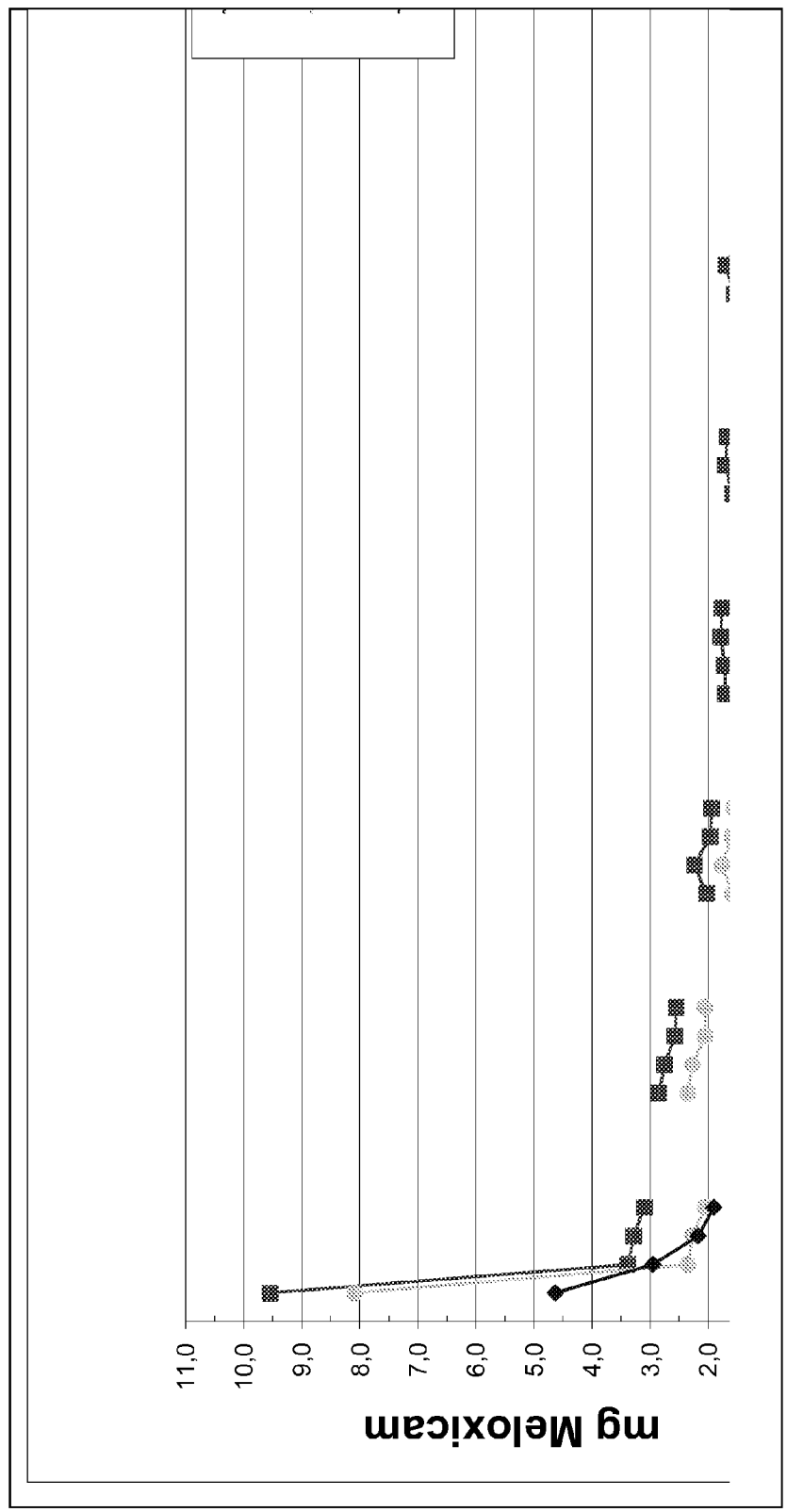
FIG. 2.—In vitro release profile of meloxicam from vaginal rings comprising 1.75 g of meloxicam with no PVP K-30 or 10% and 15% PVP K-30.
Figure 3:
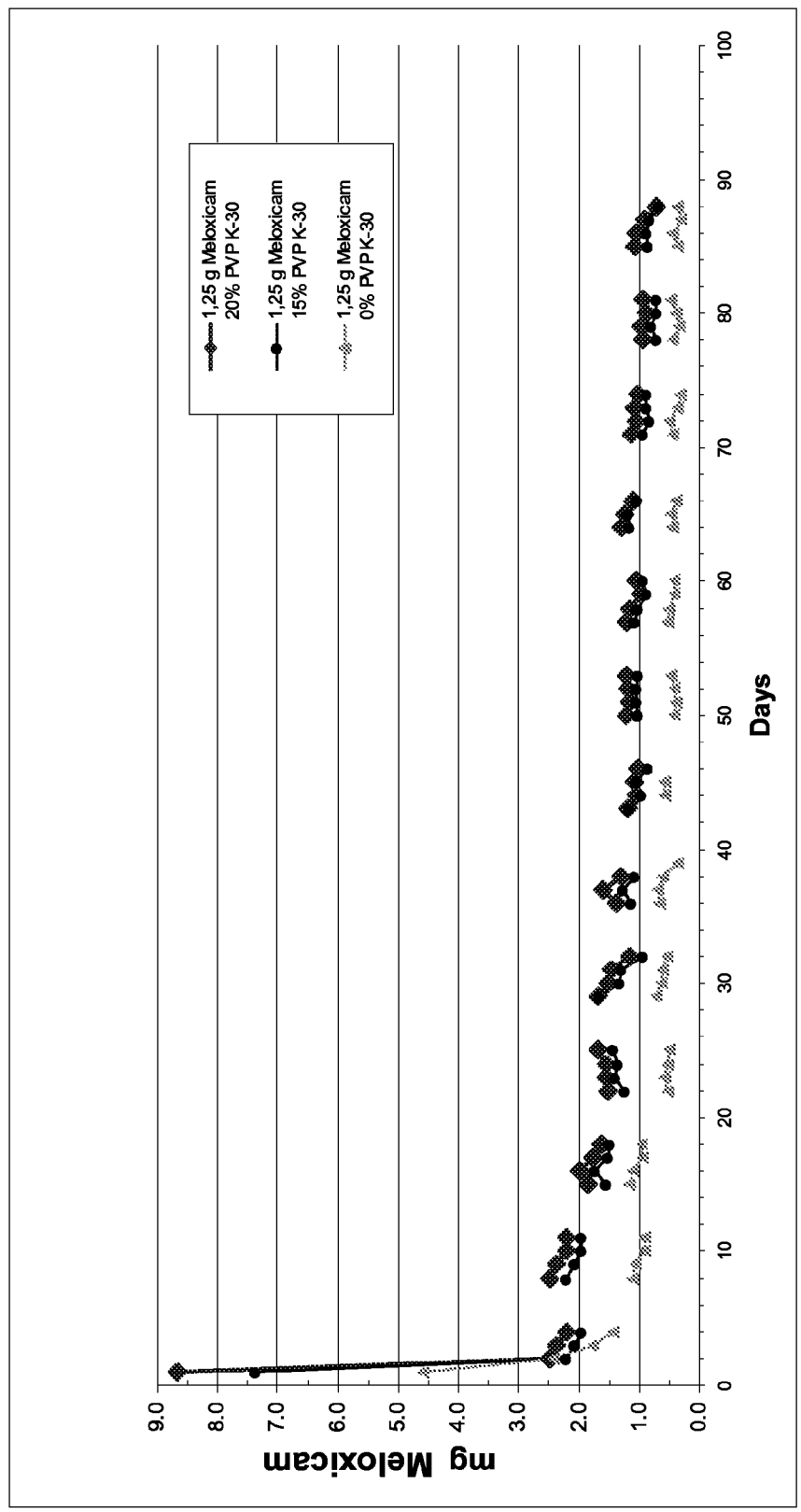
FIG. 3.—In vitro release profile of meloxicam from vaginal rings comprising 1.25 g of meloxicam with no PVP K-30 or 15% and 20% PVP K-30.

At lower doses of DHEA (1.75 g, 1.25 g), the same effect of PVP K-30 was observed, i.e., release of active principle was higher in those rings containing PVP K-30, increasing as agent concentration increased (FIGS. 2 and 3). Additionally, in the rings with lowest doses of meloxicam (1.25 mg meloxicam) saturation of the PVP K-30 effect was observed, as reflected in FIG. 3, where there was no clear difference in the release of meloxicam for 15% (SF-9) (circles) and 20% (SF-10) (diamonds) of PVP K-30.

2.3.—High Doses of Meloxicam in the Absence and Presence of Various Concentrations of PVP K-30

In addition, rings containing high doses of meloxicam (3.0 g) in the absence (SF-20) and in the presence of PVP K-30 (SF-21 and SF-22) were assayed. In these cases the rings not containing PVP K-30 released a higher amount of meloxicam (5.94 mg) between days 1 to 4 compared with what was observed with rings with 5% (SF-21) and 10% PVP K-30 (SF-22) corresponding to 4.55 mg and 4.96 mg (FIG. 4, gray bars), respectively. This effect can be given for the high amount of active agent with no agent contained in the crosslinked structure of the polymer ring to modulate the release of the drug, leaving a large mass of active principle available to be released immediately In the following days (5-30 days), meloxicam release from the rings also increased as PVP K-30 concentration increased, being 2.01 mg, 2.31 mg and 2.8 mg for 0%, 5% and 10% PVP K-30, respectively (FIG. 5, gray bars). Similarly, at longer periods of time (31-90 days), a significant release of meloxicam from these rings was still observed, achieving 1.07 mg, 1.55 mg and 2.04 mg for PVP K-30 concentrations of 0%, 5% and 10% (FIG. 6, gray bars).

Figure 7:
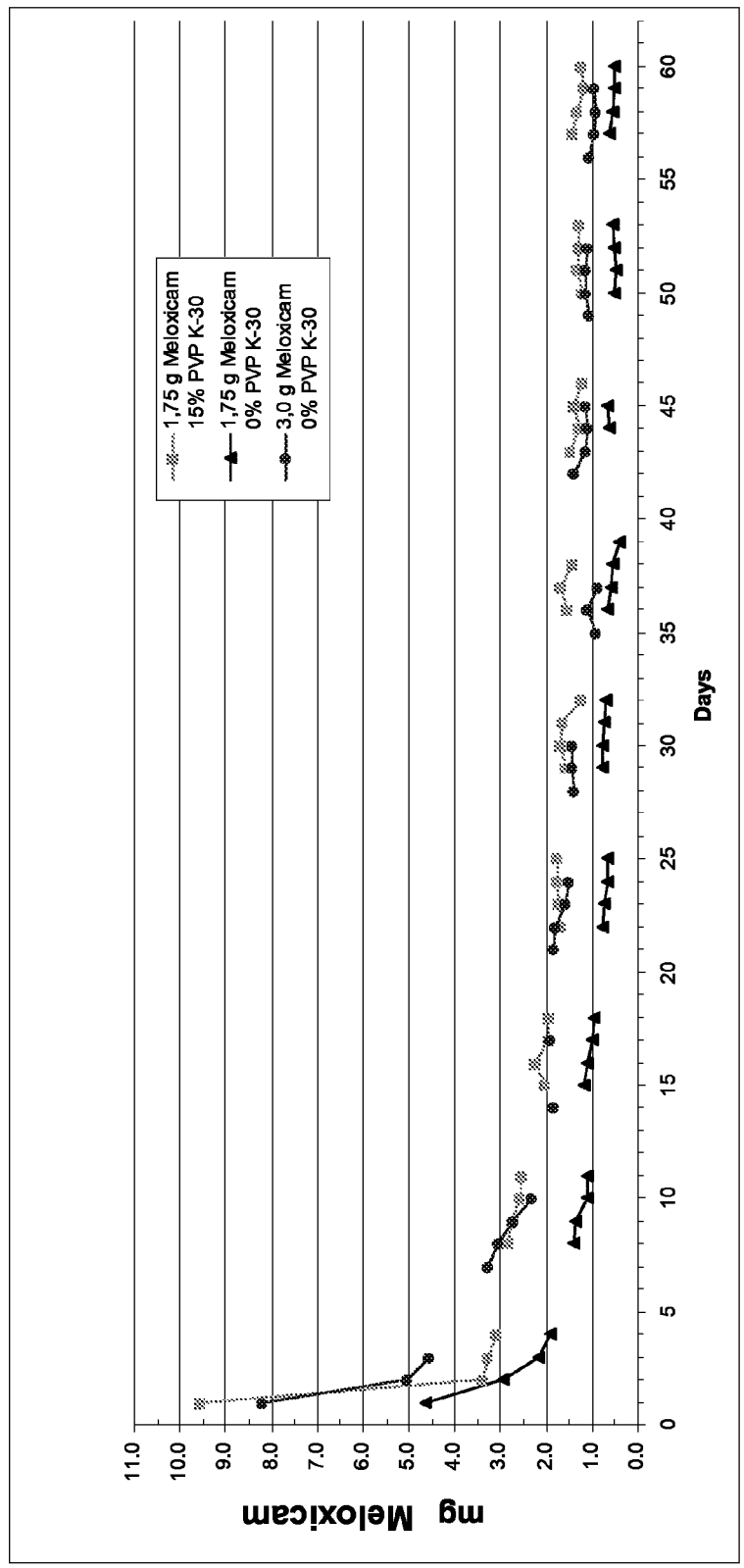
FIG. 7.—In vitro release profile of meloxicam from vaginal rings comprising 1.75 g to 3.0 g of meloxicam with no PVP K-30 and from rings comprising 1.75 g of meloxicam with 15% PVP K-30.

The 3.0 g meloxicam dose was the highest dose assayed and accordingly was the dose with which a higher release of meloxicam was obtained, with or with no PVP K-30. The release observed with 3.0 g meloxicam with no PVP K-30 was achieved by a low dose of meloxicam (1.75 g) in the presence of 15% PVP K-30 (SF-14, Table 3). This effect is observed in FIG. 7, where the release from rings was compared with 1.75 g of m meloxicam in the absence (SF-11) (triangles) or in the presence of 15% (SF-14) PVP K-30 (squares) with rings containing 3.0 g of meloxicam with no PVP K-30 (circles).

Figure 4:
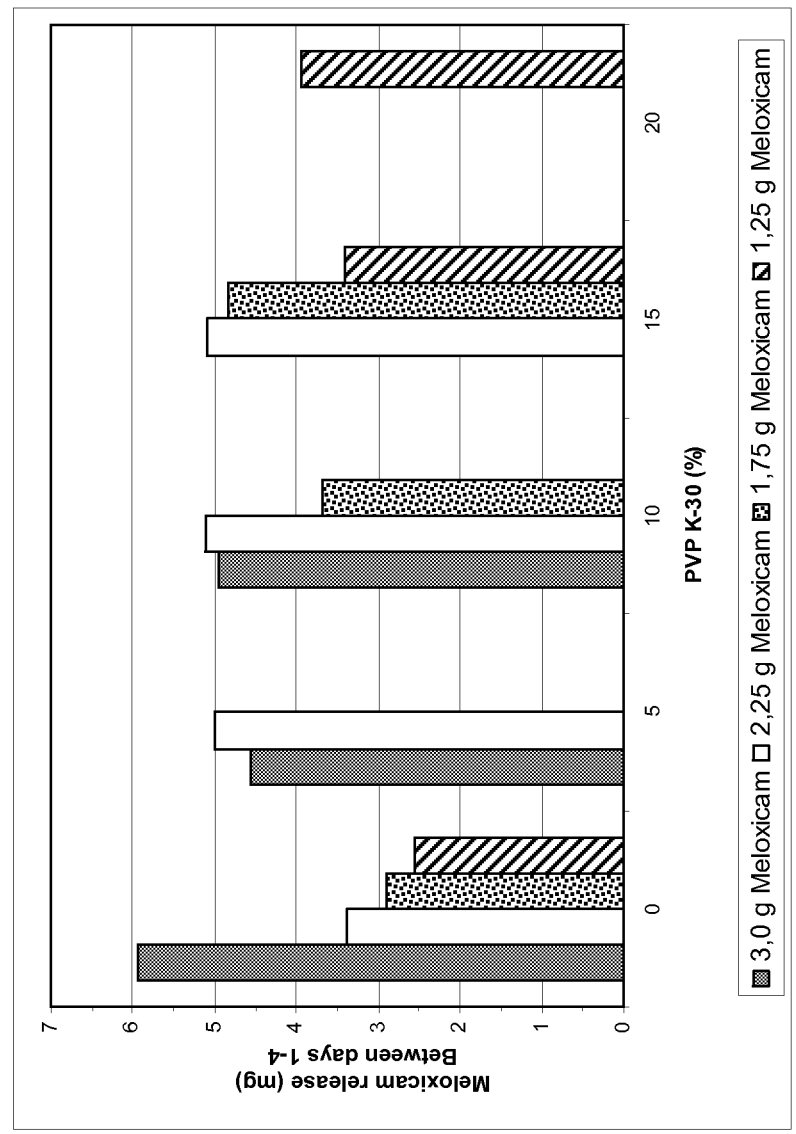
FIG. 4.—Profile of mean in vitro release of meloxicam between days 1 to 4 from vaginal rings comprising 3.0 g, 2.25 g, 1.75 g and 1.25 g of meloxicam with no PVP K-30 or 5%, 10%, 15% and 20% PVP K-30.
Figure 8:
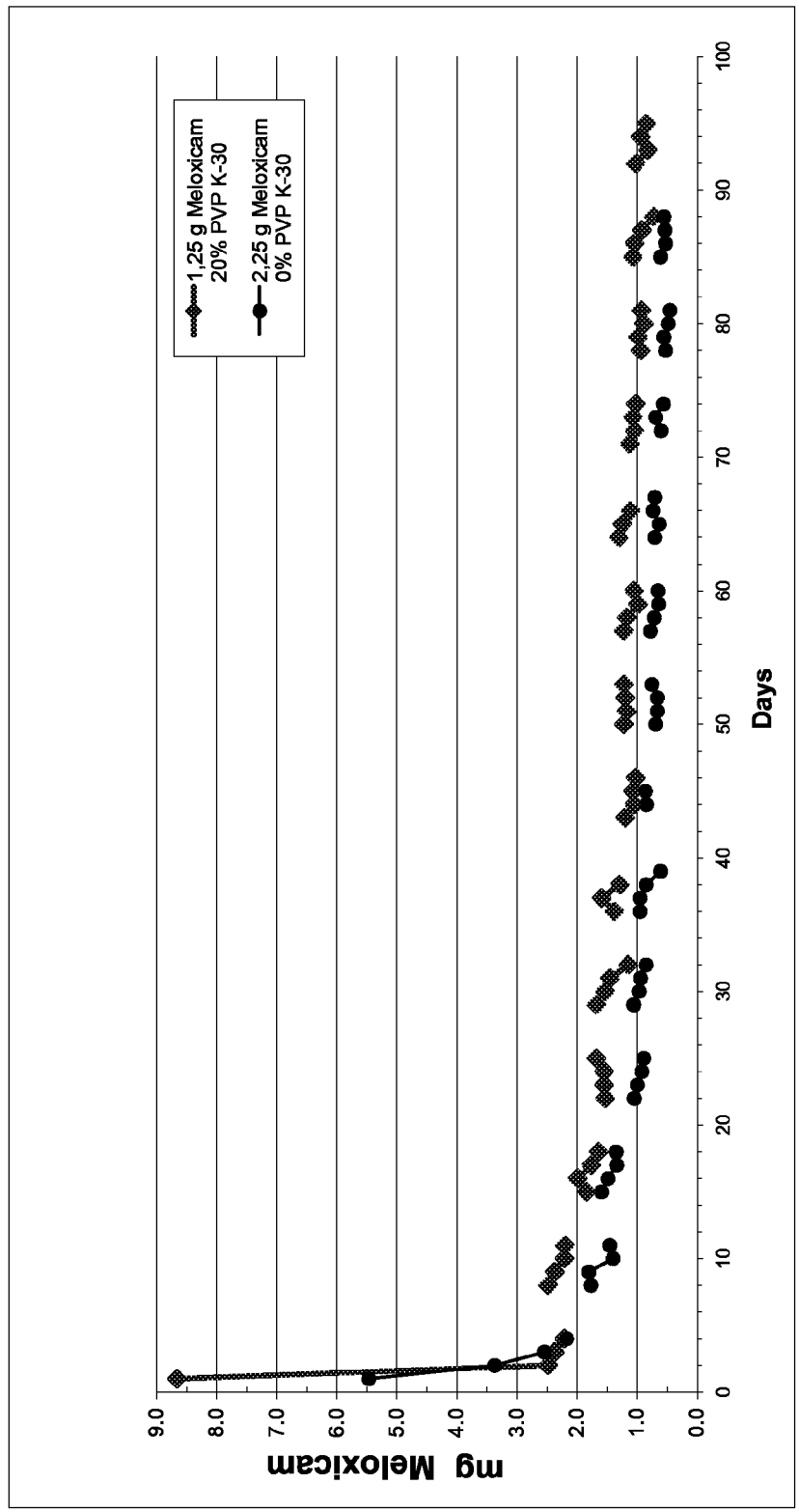
FIG. 8.—In vitro release profile of meloxicam from vaginal rings comprising 2.25 g of meloxicam with no PVP K-30 and from rings comprising 1.25 g of meloxicam with 20% PVP K-30.

Similarly, the level of release of the rings containing 2.25 g of meloxicam with no PVP K-30 was lower than the release from rings containing lower doses of meloxicam (1.25 g) with 20% PVP K-30 (SF-10), as seen in FIG. 8 and as compared in FIGS. 4, 5 and 6, white bars (0% PVP K-30) versus hatched bars (15% and 20% PVP K-30).

2.4.—Others Modifying Agents for Active Principle Release

Figure 9:
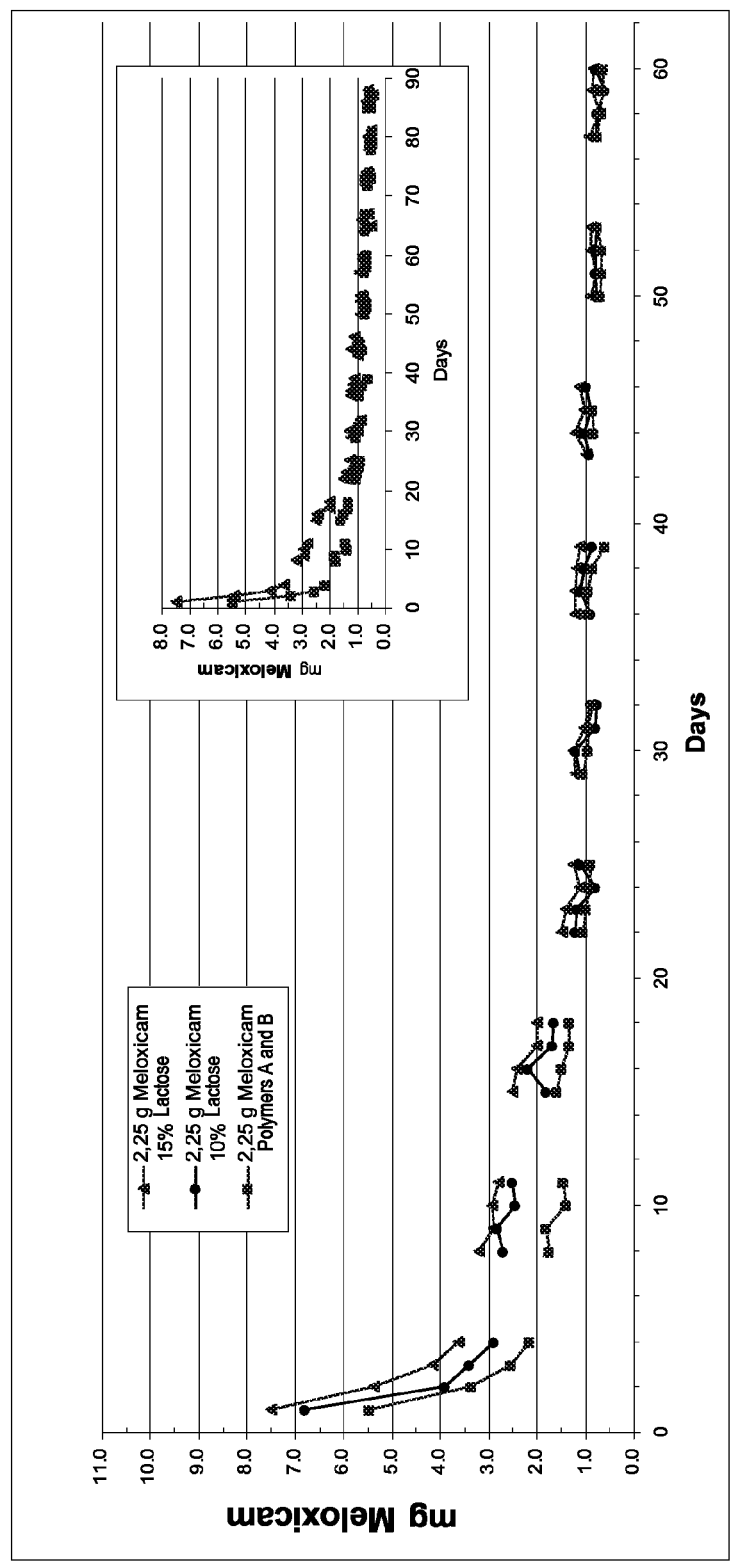
FIG. 9.—In vitro release profile of meloxicam from vaginal rings comprising 2.25 g of meloxicam with no lactose or with 10% and 15% of lactose.

Rings containing meloxicam at doses of 1.75 g 2.25 g with 10% of lactose (SF-25 and SF-27), 15% of lactose (SF-26 and SF-28), 5% of microcrystalline cellulose (SF-29 and SF-31) or with 15% of microcrystalline cellulose (SF-30 and SF-32), released a higher amount of meloxicam in short periods of time compared to rings containing meloxicam but with no lactose or no microcrystalline cellulose; achieving the same release levels than the latter ones in longer periods of time. In FIG. 9 the effect of 10% and 15% of lactose producing an increased release of meloxicam from the rings between days 1-19 is observed; but between days 21-90 release levels were indistinguishable between rings with and with no lactose.

Figure 10:
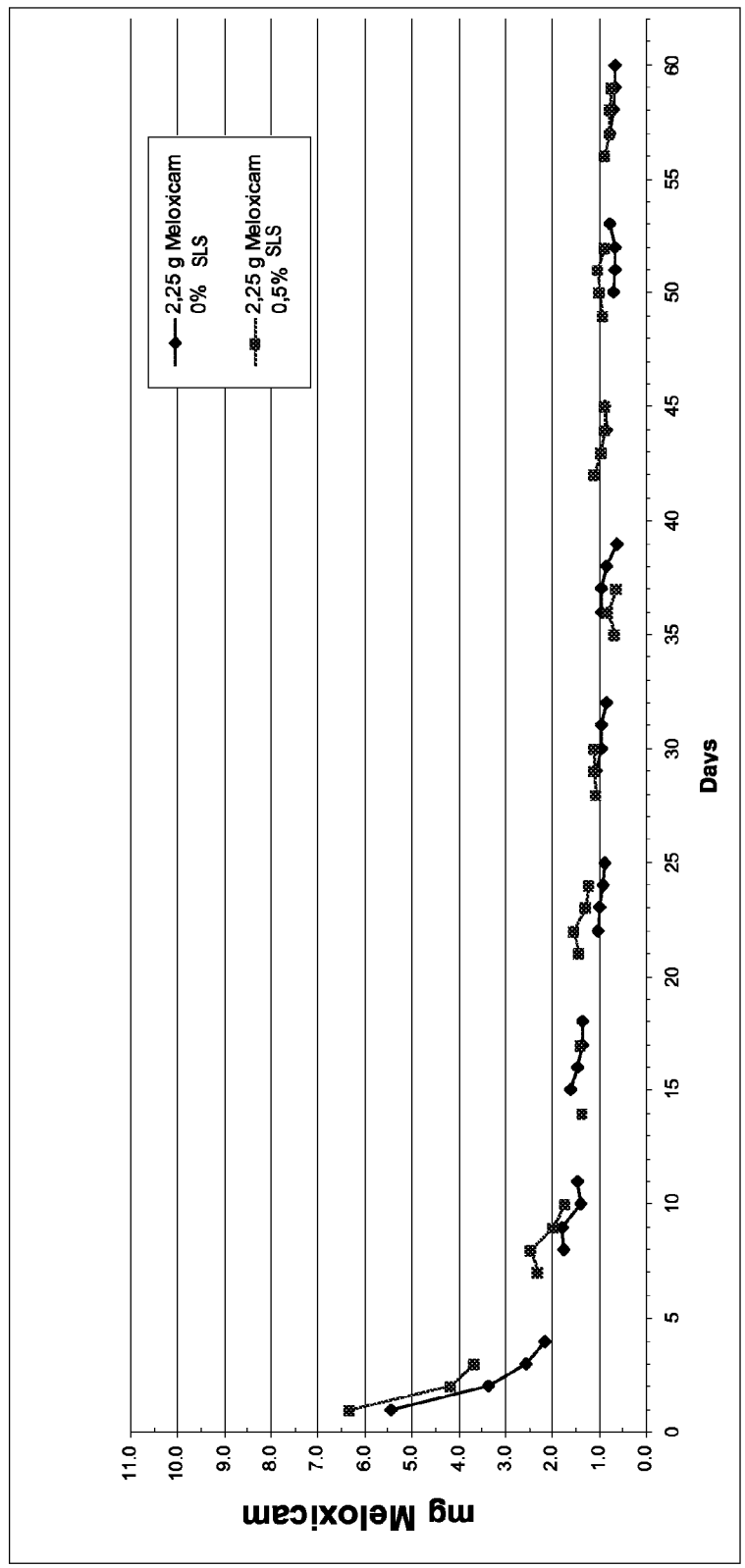
FIG. 10.—In vitro release profile of meloxicam from vaginal rings comprising 2.25 g of meloxicam with no sodium lauryl sulfate (SLS) or with 0.5% SLS.

Rings containing 2.25 g of meloxicam with 0.1% (SF-23) or 0.5% (SF-24) of sodium lauryl sulfate also released a higher amount of the drug than rings not containing sodium lauryl sulfate, but only in short periods of time (days 1-8). Between days 9 to 60 no differences were observed between the rings with and without the agent, as shown in FIG. 10 for rings containing 0.5% of sodium lauryl sulfate and rings not containing sodium lauryl sulfate.

Higher concentrations of SLS (1%) were also assayed, but the rings did not properly cured so they were discarded.

From these results we conclude that only with PVP K-30 is possible to achieve a higher release of active principle compared with rings not having the agent both in short periods of time as in long periods of time (up to at least 90 days). With none of the tested agents a similar effect was obtained, either rings did not cured during polymerization step of manufacture or showed no differences of release in long periods of time.

The highest release of meloxicam from rings containing PVP K-30 as a release-modulating agent was sustained over time even up to 90 days, being that release always higher than of those not containing this agent.

These results are completely surprising, as there was nothing that predicted the rings comprising PVP K-30 would present a release profile as observed, unlike all other agents tested.

2.5.—Other Polymers

Figure 11:
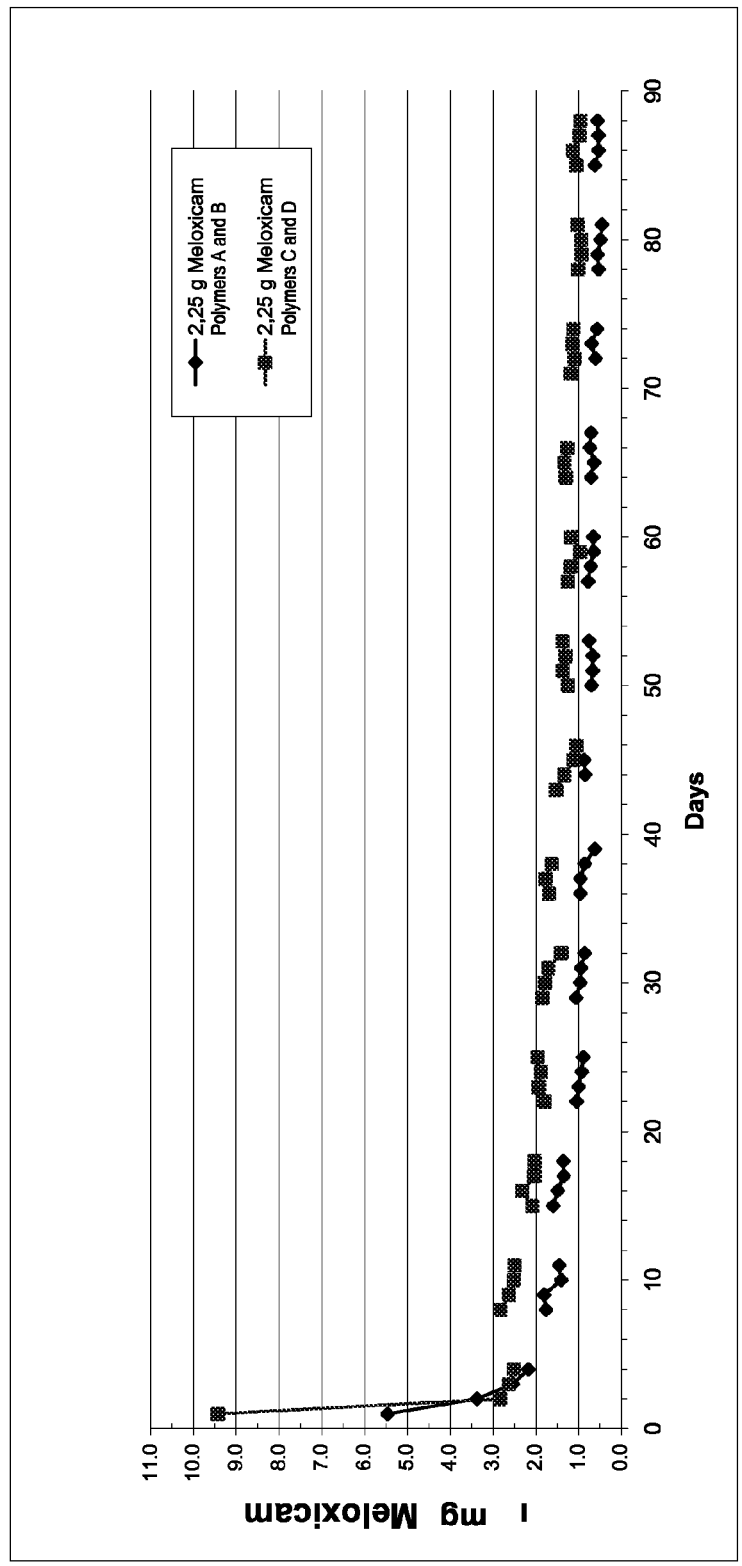
FIG. 11.—In vitro release profile of meloxicam from vaginal rings formed with Polymers A and B (GF-1, described in Table 1) and with polymers C and D (GF-10, described in Table 2) comprising 2.25 g of meloxicam with no release-modulating agent for drug release.

Rings formed by Polymer C and D (see Table 2, GF-10) comprising different doses of meloxicam with no PVP K-30 were assayed. These rings were discarded as a product recommended for human use, because of the physical properties presented (see Table 8 and below). Nevertheless, the release profile of the rings containing 2.25 g of meloxicam was evaluated and it was observed that they release a higher amount of active principle throughout the recorded period of time, compared to rings made of Polymer A and B (FIG. 11), according to GF-1 described in Table 1.

These results demonstrate that for a pharmaceutical product in the form of a vaginal ring is not enough that the rings exhibit an in vitro release profile with a high and stable active agent release rate, but should also possess suitable physical characteristics, among others factors, to meet the requirements of acceptability of a finished product.

3.—Physical Properties of Rings

Vaginal rings comprising meloxicam, in addition to possess the necessary releasing characteristics of the active principle to reach tissue levels allowing to achieve the therapeutic effect must have other properties that make it suitable for intravaginal administration, besides certain acceptability requirements for users. Among these, the ring must be flexible so that the user can press it in order to give the necessary form to insert into the vagina. In addition, the ring must have a uniform smooth surface, smooth to the touch, with no stickiness and regular consistency, i.e., with a certain softness to facilitate its application.

Rings were assayed at different doses of meloxicam containing different release-modulating agents of the active principle in various concentrations. In these rings consistency (hardness), flexibility, porosity, stickiness and brightness properties were evaluated.

Rings comprising meloxicam with PVP K-30 as a release-modifying agent had different physical properties depending on the concentration of this agent and the amount of meloxicam in the ring. The addition of PVP K-30 gradually increased hardness, reducing flexibility and increasing the porosity of these. Furthermore, at high doses of PVP K-30 and meloxicam the stickiness of rings markedly increased.

These observations are clearly seen in Table 8, where meloxicam concentrations used with the release-modulating agent of active principle are listed.

Correspondingly with the properties that intravaginal administration rings must possess, those with higher consistency were discarded, had no brightness, were little or no flexible and were clearly porous and sticky. In consequence, rings comprising high concentrations of meloxicam and/or PVP K-30 are not suitable for intravaginal administration, i.e., rings with 3.0 g of meloxicam and 5% or 10% PVP K-30, rings with 2.25 g of meloxicam and 15% PVP K-30.

The other release modifiers that were assayed also altered physical properties of the rings containing meloxicam. Lactose containing rings showed a high consistency, i.e., higher hardness, than rings with PVP K-30 at the same meloxicam dose, as observed by comparing the data from Table 8 with Table 9. Flexibility of the rings containing 2.25 g of meloxicam and lactose was much lower than that of the rings containing 1.75 g of meloxicam with the same agent (10% or 15%). Rings with lactose had high porosity and a low level of brightness and stickiness. Considering only physical properties, rings containing high doses of meloxicam (2.5 g) and lactose (10% or 15%) are not recommended as final product (Table 9).

TABLE 8

| RING COMPOSITION | | | PHYSICAL PROPERTIES | | | | | QUALIFICATION Recommendation based on physical appearance |
|---|---|---|---|---|---|---|---|---|
| Meloxicam (g) | Modulating agent | Modulating Agent (%) | Consistency | Brightness | Flexibility | Porosity | Stickiness | |
| 1.25 | No | 0 | + | +++ | +++ | − | − | Yes |
| 1.25 | PVP K-30 | 15 | ++ | ++ | ++ | + | + | Yes |
| 1.25 | PVP K-30 | 20 | +++ | + | ++ | +++ | + | Yes |
| 1.75 | No | 0 | + | +++ | +++ | − | − | Yes |
| 1.75 | PVP K-30 | 10 | ++ | ++ | ++ | − | − | Yes |
| 1.75 | PVP K-30 | 15 | ++ | + | ++ | +++ | + | Yes |
| 2.25 | No | 0 | ++ | +++ | ++ | − | − | Yes |
| 2.25 | PVP K-30 | 5 | ++ | ++ | ++ | + | + | Yes |
| 2.25 | PVP K-30 | 10 | ++ | + | ++ | + | + | Yes |
| 2.25 | PVP K-30 | 15 | +++ | + | + | +++ | ++ | No |
| 3 | No | 0 | ++ | +++ | ++ | + | + | Yes |
| 3 | PVP K-30 | 5 | +++ | ++ | + | +++ | ++ | No |
| 3 | PVP K-30 | 10 | +++ | ++ | + | +++ | ++ | No |
| 2.25 (*) | No | 0 | ++++ | ++ | + | +++ | ++ | No |

(*) These vaginal rings were prepared with polymer DDU 4340, according to General Formula 11 (FG-11) listed in Table 2.

TABLE 9

| RING COMPOSITION | | | | | | | | QUALIFICATION |
|---|---|---|---|---|---|---|---|---|
| | | Modulating agent | PHYSICAL PROPERTIES | | | | | Recommendation based on |
| Meloxicam (g) | Modulating agent | (%) | Consistency | Brightness | Flexibility | Porosity | Stickiness | physical aspect |
| 1.75 | Lactose | 10 | ++ | ++ | ++ | ++ | + | Yes |
| 1.75 | Lactose | 15 | +++ | + | ++ | +++ | + | Yes |
| 2.25 | Lactose | 10 | +++ | + | + | ++ | + | No |
| 2.25 | Lactose | 15 | +++ | + | + | +++ | + | No |
| 1.75 | microcrystalline cellulose | 5 | + | ++ | ++ | ++ | − | Yes |
| 1.75 | microcrystalline cellulose | 15 | +++ | + | ++ | ++ | + | Yes |
| 2.25 | microcrystalline cellulose | 5 | ++ | ++ | ++ | +++ | − | Yes |
| 2.25 | microcrystalline cellulose | 15 | +++ | + | + | +++ | + | No |
| 2.25 | SLS | 0.1 | ++ | ++ | ++ | + | − | Yes |
| 2.25 | SLS | 0.5 | ++ | + | ++ | + | − | Yes |

Meloxicam and microcrystalline cellulose rings had physical consistency, flexibility, stickiness and brightness properties, suitable for being administered transvaginally even when they showed some degree of porosity; except rings with high doses of meloxicam (2.5 g) and microcrystalline cellulose (15%), which were not recommended as final product because of its high consistency (hardness) and high porosity (rough surface) (Table 9).

Rings containing 2.25 g of meloxicam and 0.1% or 0.5% sodium lauryl sulfate (SLS) were also assayed. Under both conditions the rings had good physical properties (Table 9), so considered only these parameters they would be recommended as final product.

In addition, alternative polymers used for rings manufacturing (polymers C and D, as defined in Table 2) also affected the physical properties thereof. In the manufacturing process when injecting the molds, it was observed that the mixture containing these polymers was remarkably more consistent and viscous than the mixtures with the other polymers (polymers A and B), making difficult injecting and filling the molds because of the pressure that had to be exerted. The rings polymerized (cured) but were very rigid, hard and less flexible, making it difficult to maintain them folded simulating the condition of intravaginal application. Therefore, because of the high consistency (hardness), poor flexibility, certain porosity and stickiness (Table 8), these rings are not suitable as a final product.

4.—Meloxicam In Vivo Release Studies

For evaluating vaginally release and absorption of meloxicam in vivo, 3 vaginal rings with different formulations were administered in six healthy women volunteers between 28 and 42 years old and had regular menstrual cycles of 28-32 days. Plasma and endometrial levels of the active agent were measured after administration of meloxicam containing rings with or without the modulating agent.

The rings used in this study contained: 1) 1.75 g de meloxicam with no modulating agent; 2) 2.25 g of meloxicam with no modulating agent; y 3) 1.75 g of meloxicam plus 15% PVP K-30. Each one if these rings were administered in two volunteers. These doses of active and modulating agents were chosen for studies in vivo because in vitro release studies showed a marked difference between them in the released amount of meloxicam, throughout the recorded period of time (1-90 days), and also by the excellent physical properties of the respective rings. All these features made them recommendable as potential final products.

Women installed vaginal rings on day 5 of their menstrual cycle, day 1 being the day on which the bleeding started. Blood samples from each volunteer were taken at the following times (in hours post-administration of the ring): 4, 6, 8, 10, 24, 36, 48, 60, 72, 84, 96, 108, 120, 204, 372, 540 and 708. Endometrial biopsies were also taken at 4 and 36 hours post-administration, and subsequently on days 9 (204 hours), 16 (372 hours), 23 (540 hours) and day 30 (708 hours). All volunteers removed the ring at the beginning (start of the bleeding) of the next menstrual cycle (between days 23 and 27) and insert it again on day 5 of the second cycle.

The effect of vaginal ring with meloxicam on the menstrual cycle of women has a significant difference from hormonal contraceptive rings. The removal of the hormonal ring available in the market causes a sharp decrease of estrogen and progestin levels, generating a pharmacological menstruation caused by hormone deprivation. Instead, the ring with meloxicam is removed when spontaneously and physiologically the next menstrual period starts, which is produced with no hormonal alterations. Added to this, there is no need for the user to recall the time to remove the ring with meloxicam, since the first day of her menstrual cycle (first day of bleeding) indicates that it is time to have it removed for reinserting the same ring or a new one on the 5th day of that cycle.

Figure 12:
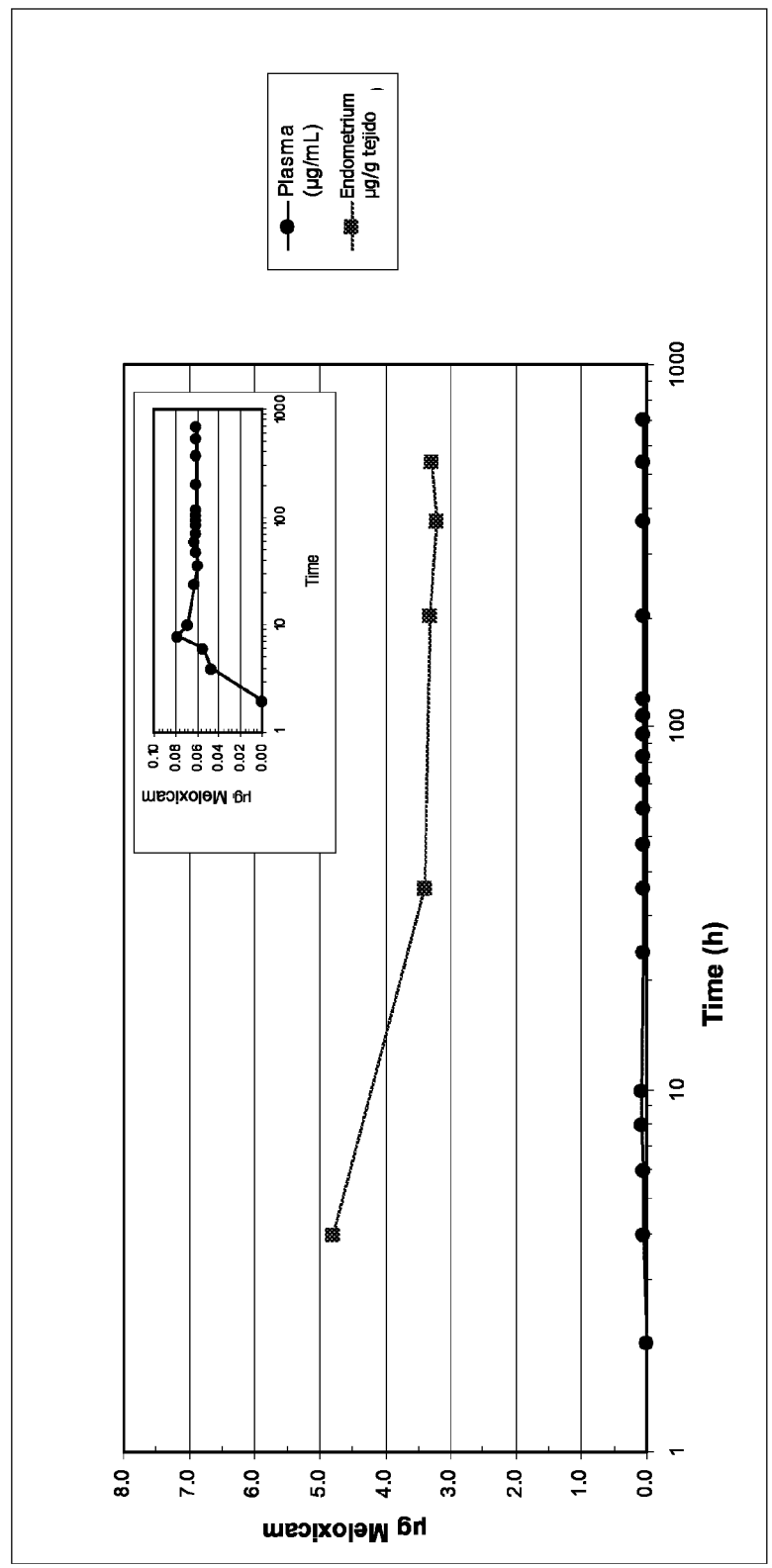
FIG. 12.—Plasma meloxicam levels in women plasma and endometrial tissue, after administration of vaginal rings comprising 1.75 g of meloxicam with no release-modulating agent for drug release.

In FIG. 12 is shown plasma and endometrial meloxicam levels obtained after administration of rings with 1.75 g of meloxicam with no modulating agent. The quantity of meloxicam in plasma was very low (circles) and only a maximum near 0.08 g/mL was obtained. This is clearly seen in the insert box of FIG. 12 which corresponds to an extension of axis OY. In contrast, the meloxicam levels in tissue (squares) were significantly higher, achieving values close to 5 μg/g of tissue. Both in plasma and endometrium was observed a constant level in the meloxicam release after 36 hours post-administration of the ring, achieving values of 0.06 μg/ml (plasma) and 3.5 μg/g of tissue (endometrium). This behavior was keep until the last day of sampling (day 30 (708 hours) and 23 (540 hours) for plasma and tissue, respectively). It was not possible to take an endometrial biopsy on day 30, as most women being in the early days of their second cycle were bleeding. The ring had been removed by volunteers when the bleeding of this second cycle started, as indicated. The volunteers remained with the intravaginal ring for a period between 1-3 months and reported ease of inserting and ease of removal. Even women who used it for 3 months reported that they were able to removed it at the beginning of the next period after its initial insertion and reinserted it at the end of menstruation (pre-set as day 5) to continue therapy.

Figure 13:
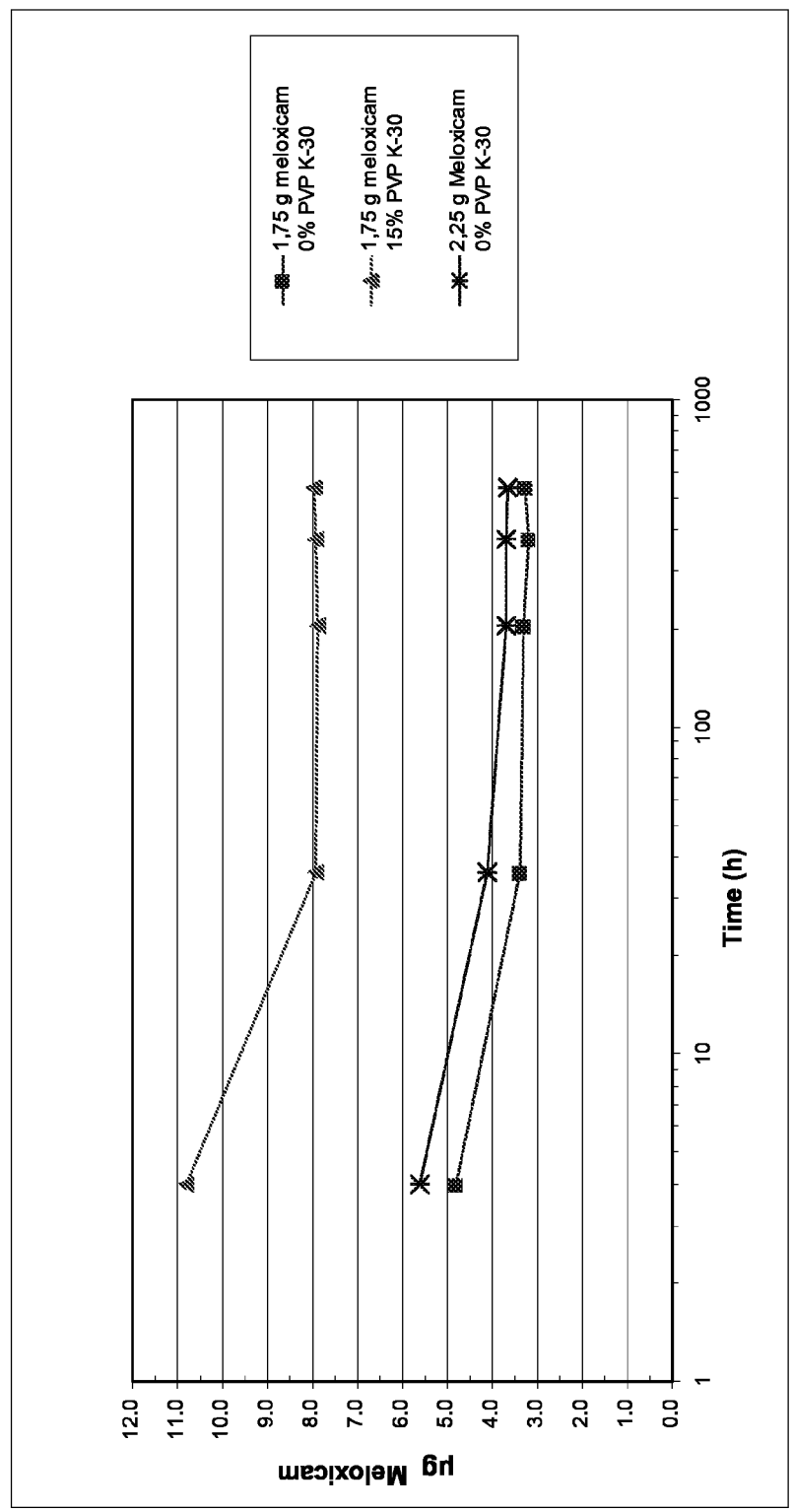
FIG. 13.—Meloxicam levels in women endometrial tissue after administration of vaginal rings comprising 1.75 g and 2.25 g meloxicam with no PVP K-30 and 1.75 g of meloxicam with 15% PVP K-30.

Endometrial meloxicam levels obtained after administration of rings containing 1.75 g of meloxicam and 15% PVP K-30 were higher than with rings with no PVP K-30. In FIG. 13 is clearly distinguishable this effect. When rings containing the modulating agent were administered, the amount of meloxicam in samples was, on average, 2.4 times higher (triangles) than with rings with no modulating agent (squares). Moreover, the rings containing 1.75 g of meloxicam with 15% PVP K-30 (triangles) induced an average increase of 2.1 times higher than the rings containing 2.25 g of meloxicam with no modulating agent (crosses). From these results it was possible to distinguish a peak on meloxicam levels in the endometrium 4 hours post-administration of the vaginal ring. It is likely that the peak does not occur exactly at this time, which may have been hidden due to low number of possible endometrial biopsies obtained from women. Even so, the results are conclusive and indicate that the amount of meloxicam that reach the endometrial tissue with vaginal rings containing PVP K-30 was significantly higher than with rings not containing this agent for both 1.75 and 2.25 g meloxicam rings. These results could not be predicted from the in vitro release assays (see FIG. 5), since although the increase of in vitro release of meloxicam between days 5-30 for rings containing 1.75 g of meloxicam with 15% PVP K-30 relative to the rings with no the agent, was on average 2.2 times (versus 2.4 times in endometrium), it was only 1.61 times relative to rings containing 2.25 g of meloxicam with no PVP K-30 (versus 2.1-fold in endometrium, FIG. 13). That is to say, rings with 1.75 g of meloxicam with PVP K-30 provide meloxicam levels in endometrium much higher than what was possible to predict, compared to the rings with no PVP and with higher doses of meloxicam.

Figure 14:
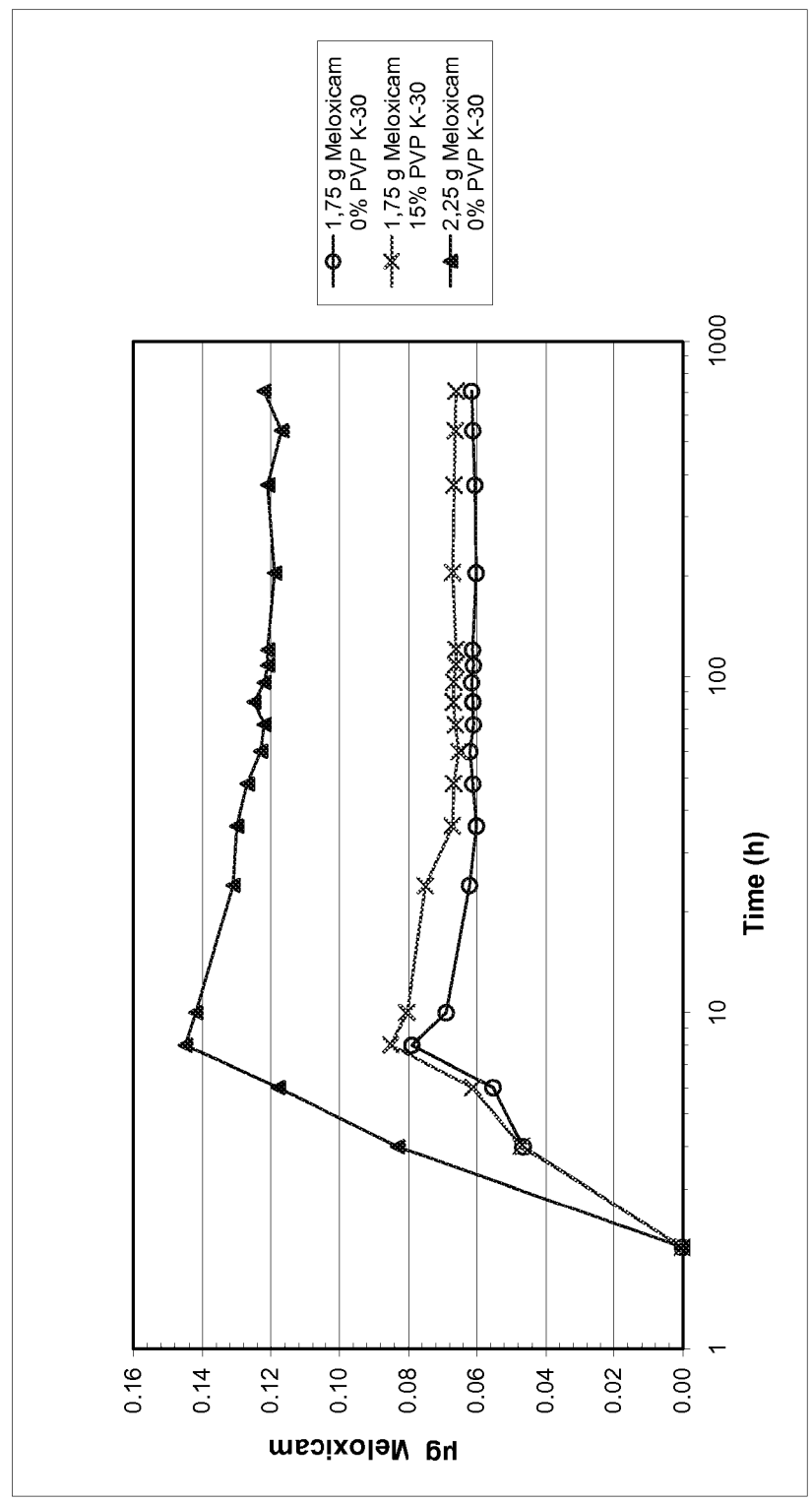
FIG. 14.—Plasma meloxicam levels in women after administration of vaginal rings comprising 1.75 g and 2.25 g meloxicam with no PVP K-30 and 1.75 g of meloxicam with 15% PVP K-30.

When measuring meloxicam levels in the plasma it was observed a different behavior to that observed in endometrial tissue. As shown in FIG. 14, although the plasma levels found were higher for the rings containing modifying agent PVP K-30 in a dose of 1.75 g of meloxicam (crosses versus circles); only an increase of 1.1 times in the amount of plasma meloxicam relative to rings with no PVP K-30 and the same dose of meloxicam (1.75 g) was observed. The results of the in vitro release (FIG. 5, dotted bars) showed 1.61-fold differences between these two types of rings. Instead, for rings with 1.75 g of meloxicam and 15% PVP K-30 could had been predicted 2.2-fold higher plasma levels compared to the rings containing higher doses of meloxicam (2.25 g) with no modifying agent, given the release behavior in vitro, (FIG. 5, 15% PVP K-30 dashed bar versus 0% PVP K-30 white bar); but the effect on the plasma levels was inverted, as they were higher (1.83 times) for rings containing 2.25 g of meloxicam than rings with 1.75 g of meloxicam and 15% PVP K-30 (FIG. 14, triangles versus crosses).

These results are completely unexpected and unpredictable, since in the in vitro release an increase in the meloxicam release in the presence of PVP-K30 was observed, which was dependant of this agent concentration in the rings. This did not allow us to project that, in vivo, a higher concentration of meloxicam would be obtained in tissue with no increasing the plasma concentration of the drug. Even, it was not possible to predict that high meloxicam concentrations into the rings without the modifying agent could increase plasma levels of the drug much more than that what was obtained with the rings with PVP K-30; instead, showed an opposite behavior at tissue level, i.e., a higher concentration of meloxicam is obtained with rings containing PVP K-30 than without this agent, even when the ring contains a higher dose of this drug.

From the results of in vitro release was expected that at same meloxicam concentration rings with PVP K-30 would provide a higher meloxicam concentration than rings with no PVP K-30, both at plasma and endometrial level, but surprising results have been obtained showing that with rings comprising PVP K-30, higher drug levels are achieved in the tissue in situ no affecting plasma concentrations.

When increasing the amount of meloxicam in the rings (no adding PVP K-30) in order to obtain higher concentrations in the endometrium, plasma drug concentration will also increase (FIG. 14). Therefore, to achieve greater tissue concentration without affecting plasma concentration in the same way is enough with co-administering meloxicam and PVP in the ring without increasing meloxicam dose in the same (FIG. 13).

When 7.5 mg of meloxicam were orally administered in the form of tablets, maximum plasma concentrations of 1.05 µg/mL at 4.9 hours were obtained (Label MOBIC®, published online at: http://www.accessdata.fda.gov/drugsatfda docs/label/2011/020938s021,021530s009lbl.pdf). With the oral administration of 15 mg tablets in older women, concentrations of 3.2 µg/mL at 6 hours were obtained. In the present invention, with the administration of intravaginal rings containing 1.75 g of meloxicam and 15% PVP K-30 a maximum plasma concentration of 0.085 g/mL at 8 hours was obtained. With these very low levels of systemic meloxicam (about 12 to 37 times lower than observed orally), administration of vaginal rings is very safe because the probability of occurrence of side effects typical of a COX-2 as meloxicam, is significantly decreased. It is worth mentioning that with the administration of the vaginal ring, known gastrointestinal effects produced by meloxicam will not occur, and the need for daily administration is eliminated, because is enough the insertion of the same ring once a month or once every two or three months.

The invention claimed is:

1. A sustained-release vaginal ring comprising a homogenous mixture of meloxicam, two polymers and polyvinylpyrrolidone K-30 as a release enhancing agent for sustained release of the active ingredient meloxicam, wherein the two polymers are a mixture of polymer A and polymer B and wherein the polymer A is polydimethylsiloxane-vinyl block polymer, amorphous silica and platinum catalyst, and polymer B is dimethyl methyl hydrogen siloxane copolymer and polydimethylsiloxane.

2. The vaginal ring according to claim 1, wherein the active ingredient is released in a sustained manner for a period of at least 90 days.

3. The vaginal ring according to claim 1, wherein the active ingredient is released in a sustained manner for a period of at least 60 days.

4. The vaginal ring according to claim 1, wherein the active ingredient is released in a sustained manner for a period of at least 30 days.

5. The vaginal ring according to claim 1, comprising 5% to 30% by weight of meloxicam, relative to the total weight of the formulation.

6. The vaginal ring according to claim 1, comprising 5% to 20% of polyvinylpyrrolidone K-30 by weight, relative to the total weight of the formulation.

7. A method for continuous contraceptive treatment comprising administering the vaginal ring according to claim 1.

8. A method for long-term contraceptive treatment comprising administering the vaginal ring according to claim 1.

* * * * *